(12) United States Patent
Wallbridge et al.

(10) Patent No.: US 10,173,059 B2
(45) Date of Patent: Jan. 8, 2019

(54) APPARATUS AND METHOD FOR PROCESSING SIGNALS

(71) Applicant: Vivent sárl, Crans-près-Céligny (CH)

(72) Inventors: Nigel Christopher Wallbridge, Crans-près-Céligny (CH); Carrol Annette Plummer, Crans-près-Céligny (CH); Martin Timms, Northumberland (GB); Caleb Carroll, Cochrane (CA); Nicholas Barker, Durham (GB)

(73) Assignee: VIVENT SÁRL, Crans-Près-Céligny (CH)

( * ) Notice: Subject to any disclaimer, the term of this patent is extended or adjusted under 35 U.S.C. 154(b) by 0 days.

(21) Appl. No.: 14/898,203

(22) PCT Filed: Jun. 13, 2014

(86) PCT No.: PCT/EP2014/062457
§ 371 (c)(1),
(2) Date: Dec. 14, 2015

(87) PCT Pub. No.: WO2014/198943
PCT Pub. Date: Dec. 18, 2014

(65) Prior Publication Data
US 2016/0144173 A1 May 26, 2016

Related U.S. Application Data

(60) Provisional application No. 61/835,144, filed on Jun. 14, 2013.

(51) Int. Cl.
*A61N 1/36* (2006.01)
*A61N 1/372* (2006.01)

(52) U.S. Cl.
CPC ..... *A61N 1/36014* (2013.01); *A61N 1/37252* (2013.01)

(58) Field of Classification Search
CPC .......................... A61N 1/36014; A61N 1/0456
See application file for complete search history.

(56) References Cited

U.S. PATENT DOCUMENTS

2004/0173220 A1* 9/2004 Harry .................. A43B 3/0005
128/892
2006/0076981 A1 4/2006 Sanduleanu
(Continued)

FOREIGN PATENT DOCUMENTS

EP 2514480 A2 10/2012
GB 1344386 A 1/1974
(Continued)

OTHER PUBLICATIONS

EP14739054.6; Communication pursuant to Article 94(3)EPC; dated Nov. 6, 2018, 5 pages.

*Primary Examiner* — Paula J Stice
(74) *Attorney, Agent, or Firm* — Robert L. Wolter; Beusse, Wolter, Sanks & Maire PLLC

(57) ABSTRACT

An apparatus comprising: an electrical signal generation device configured to generate a first electrical signal, the first signal being based upon captured or expected data related to one or more human or animal subjects; and an electrical signal application device configured to apply the first electrical signal in a processed or unprocessed form to a human or animal subject.

20 Claims, 7 Drawing Sheets

(56) References Cited

U.S. PATENT DOCUMENTS

| | | |
|---|---|---|
| 2007/0073347 A1 | 3/2007 | Corbucci |
| 2007/0088405 A1 | 4/2007 | Jacobson |
| 2008/0208284 A1* | 8/2008 | Rezai .................. A61B 5/0476 607/45 |
| 2008/0215114 A1* | 9/2008 | Stuerzinger .......... A61B 5/0006 607/48 |
| 2008/0288016 A1* | 11/2008 | Amurthur .............. A61B 5/021 607/44 |
| 2009/0048503 A1 | 2/2009 | Dalal et al. |
| 2009/0095299 A1 | 4/2009 | Saldivar et al. |
| 2009/0299421 A1 | 12/2009 | Sawchuk |
| 2011/0034756 A1 | 2/2011 | Hacking et al. |
| 2011/0288605 A1 | 11/2011 | Kaib |
| 2013/0023781 A1 | 1/2013 | Freeman |

FOREIGN PATENT DOCUMENTS

| | | |
|---|---|---|
| GB | 1545849 | 5/1979 |
| WO | 1997021070 A1 | 6/1997 |

* cited by examiner

APPARATUS AND METHOD FOR PROCESSING SIGNALS

CROSS-REFERENCE TO RELATED APPLICATIONS

This application is a 371 U.S. national stage of International Application No. PCT/EP2014/062457 filed Jun. 13, 2014, which claims the benefit of U.S. Application No. 61/835,144 filed Jun. 14, 2013, and incorporated herein by reference in their entirety.

FIELD OF THE INVENTION

The present invention relates to an apparatus and method for processing signals. More particularly, but not exclusively, it relates to an apparatus and method for recording, processing and playing back signals which originate in a human or animal body. The apparatus and method has applications in diagnosis and treatment of a human or animal body.

BACKGROUND

Pharmaceutical therapies are known for the treatment of a large number of conditions. However, the development of pharmaceutical therapies typically involves significant investment and significant risk. A small number of discovered compounds (e.g. 1 in 10,000) becomes an approved pharmaceutical product or drug. Moreover, a significant amount of expenditure is required at early stages of drug development, when eventual viability of the drug cannot be guaranteed. For example, the development of a new drug may take around 10 years. Even once developed and approved for marketing, only a small proportion of drugs (e.g. 3 in 20) generate sufficient revenue for their development costs to be recovered.

Alternative therapies exist for the treatment of some conditions. For example, transcutaneous electrical nerve stimulation (TENS) uses electrical impulses to stimulate nerves in order to relieve pain symptoms. However, the efficacy of TENS is disputed, and any claimed benefit is generally limited to a small number of chronic musculoskeletal conditions.

Further, the use of electrotherapy methods, for example cranial electrotherapy stimulation (CES) are also known. CES involves the application of a small pulsed electric current across a patient's head for treatment of conditions such as anxiety, depression, insomnia and stress. However, the safety and effectiveness of methods such as CES are also disputed.

It would therefore be beneficial to provide a system and method which could be applied to diagnosis and/or treatment of the human or animal body which did not suffer from one or more of the disadvantages of known therapeutic systems and methods.

SUMMARY OF THE INVENTION

It is an object of this invention to provide an alternative delivery mechanism for therapies or treatments. It is a further object of this invention to provide an alternative discovery and/or development mechanism for therapies or treatments. Generally, it is an object of the invention to provide novel methods for generating, processing and applying electrical signals.

According to a first aspect of the invention there is provided an apparatus comprising: an electrical signal generation device configured to generate a first electrical signal, the first signal being based upon captured or expected data related to one or more human or animal subjects; and an electrical signal application device configured to apply the first electrical signal to a human or animal subject.

The application of the first electrical signal to a subject, where the first electrical signal is based upon captured data allows a state (e.g. an emotional state, a metabolic state, a physical state or a physiological state) of the subject to be altered. For example, by capturing data when the subject is in a desired state (e.g. sleep) and subsequently applying a signal based upon the captured data to the subject when the subject is not in the desired state (i.e. when the subject was awake), the desired state can be induced. Such data capture and subsequent application allows desired states to be induced, or less desirable states to be altered for the benefit of the subject. Further, data captured from a first subject can be applied to a second subject, allowing the first subject to 'donate' a signal which is in some way characteristic of a beneficial state to the second subject for the benefit of the second subject.

The apparatus may be configured to receive one or more input signals generated from said one or more human or animal subjects and to generate said first signal based upon said one or more input signals.

The apparatus may be configured to receive a plurality of input signals, each of said plurality of input signals being a signal captured from a respective one of a plurality of subjects. Each of the plurality of subjects may have a common characteristic. The first signal may be generated based upon the plurality of received signals.

Capturing signals from a plurality of subjects allows signals to be donated from several subjects to a single subject. For example, if each of the subjects from which signals are captured shares a common desirable characteristic (e.g. they do not smoke), a subject who is attempting to achieve that desirable characteristic (e.g. to give up smoking) may benefit from receiving a signal which is based upon the donated signals. Further, the collection of signals from a plurality of subjects may allow characteristics of the signal which are associated with the common characteristic (rather than being unique to each of the subjects) to be identified and extracted.

The electrical signal generation device may be configured to generate the first electrical signal by processing the one or more input signals.

Processing the one or more input signals may comprise filtering at least one of the one or more input signals and/or combining a plurality of input signals and/or processing the one or more input signals in any convenient way.

Processing the one or more input signals may comprise: receiving a plurality of components of a signal; detecting a phase of the signal; populating a plurality of elements of an output buffer, each element being populated with a respective one of a plurality of output signal components, and each of the plurality of output signal components being based upon one or more of the plurality of components of the signal; and generating a plurality of indices for the output buffer based upon the detected phase; wherein the first electrical signal comprises a plurality of output signal components based upon said plurality of indices.

The apparatus may further comprise: an electrical signal sensor configured to obtain an input signal from a human or animal subject.

Obtaining a signal from a subject allows signals for subsequent application to a subject to be generated based upon the obtained signal. Obtaining such a signal can form part of a treatment program, allowing continued treatment of a condition.

The electrical signal sensor may be configured to obtain an input signal from a first human or animal subject and the electrical signal application device may be configured to apply the first electrical signal to said first human or animal subject.

Applying a signal to the subject from which the signal was obtained allows a simple treatment of temporary conditions. For example, a signal obtained while a subject was sleeping can be applied to the same subject at a later time when they are unable to sleep, inducing sleep.

The electrical signal application device may be configured to apply said first electrical signal to a human or animal subject different from said one or more human or animal subjects.

The apparatus may further comprise a wide area network interface coupled to said electrical signal generation device, said wide area network interface being arranged to transmit said first electrical signal to said electrical signal application device.

The use of a wide area network to allows signals to be generated at a first location (e.g. a remote server) and applied at a second location (e.g. a treatment centre, or the home of a subject). Such an arrangement allows efficient use of computing resources, by avoiding the need to have powerful computing resources located at every treatment location.

The apparatus may further comprise a wide area network interface coupled to said electrical signal generation device wherein said electrical signal sensor is arranged to provide said input signal to said electrical signal generation device via said wide area network interface.

The use of a wide area network to allows signals to be obtained at a first location (e.g. a treatment centre, or the home of a subject) and subsequently processed at a second location (e.g. a remote server). Such an arrangement allows efficient use of computing resources, by avoiding the need to have powerful computing resources located at every signal collection location.

The apparatus may further comprise a plurality of signal sensors each arranged to provide an input signal to said electrical signal generation device via said wide area network interface.

The apparatus may further comprise an electrical signal capture device wherein the electrical signal capture device is configured to convert the one or more input signals into one or more digital signals.

Conversion of signals from analogue signals to digital signals allows digital processing, compression and storage to be carried out. Such conversion reduces the requirement for complex and dedicated analogue processing circuitry. Digital processing can often be carried out using general purpose computer processors, allowing simpler and more versatile systems to be developed than those requiring significant analogue processing circuitry.

The electrical signal application device may further comprise a digital to analogue convertor configured to convert the first signal from a digital signal to an analogue signal.

The first signal may comprise a synthesised signal.

The synthesised signal may be modelled based upon the data relating to one or more human or animal subjects.

The use of modelled signals allows characteristics of a signal to be extracted, and used to generate (synthesise) signals for subsequent application to a subject. For example, whereas a signal captured from a subject may contain significant noise components, or variation, a modelled signal can recreate the useful components of a captured signal, but without any unnecessary components.

The apparatus may further comprise a monitor interface configured for connection to a monitor device, wherein the monitor interface is configured to generate an output which is indicative of the first signal or the captured or expected data related to one or more human or animal subjects.

A monitor device can provide feedback, for example to a subject undergoing a treatment, or to a skilled operator who is delivering a treatment. Such feedback allows the capture or application of signals to be monitored and controlled closely, so as to achieve a desired outcome.

The monitor device may be a display device and the output may comprise display data.

The electrical signal application device may comprise at least one electrode. The electrode may be a transcutaneous or subcutaneous electrode.

The apparatus may further comprise a secondary sensor, wherein the secondary sensor is configured to obtain a secondary input signal from a human or animal subject.

The secondary input signal may be indicative of a state of the human or animal subject.

The use of a secondary sensor allows a subject to be monitored for signs which may assist in the capture or delivery of signals. For example, the secondary sensor may provide an indication that a subject is in a desired state, or that a state has changed. Such indications can thus improve the efficacy of a treatment program.

The captured or expected data related to one or more human or animal subjects may be selected from the group consisting of electroencepthalography data, electrocardiogram data, temperature data, conductivity data, heart rate data, blood oxygen data and blood pressure data.

The apparatus may further comprise an electrical signal stimulus device, wherein the electrical signal stimulus device is configured to deliver an electrical signal stimulus to said human or animal subject while the electrical signal capture device obtains an input signal from said human or animal subject.

The electrical signal stimulus device may be configured to generate an electrical signal stimulus comprising a frequency sweep and/or a substantially constant power spectral density within a predetermined frequency band.

The application of a stimulus comprising a frequency sweep may allow characteristics of the subject to be perturbed in a controlled way, causing the subject to generate signals which can subsequently be captured for further beneficial use. The application of a stimulus comprising a substantially constant power spectral density within a predetermined frequency band (e.g. white noise) may cause signals within a subject to be emitted with a greater amplitude, allowing an improved signal to noise ratio to be achieved. Applying different stimuli may cause the signals to have different desirable characteristics.

The apparatus may further comprise a software defined radio, the software defined radio being configured to process the one or more input signals so as to extract one or more signals having a predetermined frequency component, the first electrical signal being based upon said one or more signals having a predetermined frequency component.

Software defined radio provides a convenient means by which processing can be carried out at a variety of different frequencies, without having to have analogue circuitry designed specifically for those frequencies. This simplifies the hardware requirements for a system which is intended to process signals at a variety of different frequencies.

According to a second aspect of the invention there is provided a method for inducing a desired state in a human or animal subject comprising applying a first electrical signal to the human or animal subject, the first electrical signal being based upon a signal indicative of the desired state.

Said first electrical signal may be based upon one or more electrical signals acquired from a human or animal subject.

Said human or animal subject from which said one or more electrical signals are acquired may be said human or animal subject to which said first electrical signal is applied.

Said human or animal subject from which said one or more electrical signals are acquired may be different from said human or animal subject to which said first electrical signal is applied.

The method may further comprise processing said one or more acquired signals to generate one or more donor signals, said first electrical signal being based upon said one or more donor signals, said donor signals having characteristics associated with said desired state.

The method may further comprise processing said one or more acquired signals to remove at least one source of noise.

Said processing may be based upon sensed data.

Said processing may comprise filtering said acquired data.

Said first electrical signal may be based upon synthesised data.

The desired state may be selected from the group consisting of an emotional state, a metabolic state, a physical state and a physiological state.

According to a third aspect of the invention there is provided a method for processing a signal comprising: receiving a plurality of components of the signal; detecting a phase of the signal; populating a plurality of elements of an output buffer, each element being populated with a respective one of a plurality of output signal components, each of the plurality of output signal components being based upon one or more of the plurality of components of the signal; and generating an index for the output buffer based upon the detected phase.

Processing a signal so as to generate an index to an output buffer, which is populated by input signal components allows the implementation of a form of oscillator which mimics naturally occurring periodic (but not necessarily sinusoidal) waveforms which are captured from a subject. Such a form of processing may be referred to as a loosely coupled oscillator and may, for example, be used to identify and/or extract donor signals from input signals, or to generate an output which is indicative of a state of an input signal. Such a loosely coupled oscillator can be configured to track a periodic waveform within a predetermined frequency band (i.e. not necessarily at a specific frequency) and to generate an output which is based upon that periodic waveform, but which is not a direct copy of that periodic waveform. Such processing allows input signals to be monitored, and for transitions or changes in such input signals (e.g. changes from a first state in which the signal is coherent to a second state in which the signal is chaotic) to be detected. Such processing thus provides a powerful diagnostic tool. A plurality of indices may be generated in turn, based upon the detected phase Components of the signal may be a part of the signal (e.g. one or more samples of the signal in the temporal domain).

Generating an index for the output buffer based upon the detected phase may comprise defining an ordered plurality of indices and advancing a counter through said ordered plurality of indices at a predetermined rate based upon the detected phase to generate said index by selecting one of said indices indicated by the counter.

A loosely coupled oscillator may be implemented using an index which is advanced through an ordered plurality of indices at a predetermined rate, for example by incrementing a counter, so as to index sequentially through a circular buffer.

Said predetermined rate may be determined by modifying a nominal rate based upon said detected phase.

A loosely coupled oscillator can oscillate within a frequency band, having a centre frequency which is given by a nominal rate. By modifying the nominal rate, input signals which have periodic waveforms having frequencies close to, but not necessarily exactly matching the centre frequency, can be matched by the oscillator. This allows a single oscillator to match variety of signals, and also to match signals whose frequency shifts over time.

Modifying said nominal rate may comprise holding said counter at a constant value so as to select said one of said indices indicated by said counter a plurality of times.

Modifying said nominal rate may comprise advancing said counter so as to avoid selection of at least one of said indices indicated by said counter.

Populating a plurality of elements of an output buffer based upon components of the signal may comprise: processing said received components of the signal to generate the plurality of output signal components; and storing each of the plurality of output signal components in a respective element of the output buffer.

Processing received components of the signal to generate output signal components allows an output buffer to be populated with a modified version of the input signal. Such processing can allow the removal of signal artefacts, or random fluctuations in a signal.

The method may further comprise: updating at least some of the elements of the output buffer with revised output signal components.

Updating at least some of the elements of the output buffer may comprise; receiving further components of the signal; and processing said received further components of the signal; wherein each of the revised output signal components is based upon one or more of the plurality of components of the signal and one or more of the further components of the signal.

Updating the output buffer based on further components of the signal allows a modified version of the input signal, which is stored in the output buffer, to be revised, so as to gradually reduce the effect of fluctuations which may be present in each occurrence of a periodic waveform. For example, the output buffer may, after several occurrences of a periodic waveform within the input signal, contain a model of the periodic waveform which is an average, having contributions from each of the occurrences of the periodic waveform.

Updating at least one of the plurality of elements of the output buffer may comprise generating an average based upon one or more of the components of the signal and one or more of the further components of the signal.

The average may be a weighted mean.

The method may further comprise: storing the plurality of signal components in an input buffer; wherein detecting the phase of the signal is based upon the contents of said input buffer.

Detecting the phase of the signal based upon the contents of the input buffer (e.g. a buffer arranged to operate as a shift register) allows the index to be generated so as to maintain the output buffer in phase with the signal.

The method may further comprise: determining a property of the signal based upon a relationship between the plurality of output signal components and the signal.

The determined property of the signal may be the coherence of said signal with the plurality of output signal components.

Detecting the coherence of the signal based upon the output signal components allows changes in the input signal to be monitored (the output signal components being based on earlier components of the input signal), and thus allows the detection of changes within a subject being monitored.

The method may further comprise generating an output signal, the output signal comprising the plurality of output signal components.

The signal may be processed by a software defined radio, the processing comprising extracting one or more signals components having a respective predetermined frequency from the signal, the plurality of signal components being based upon said one or more signal components having a respective predetermined frequency.

According to a fourth aspect of the invention there is provided a method of identifying a transition in a human or animal subject between a first state and a second state, the method comprising: processing a signal obtained from said human or animal subject at a plurality of points in time to determine a property of said signal; identifying said transition in the subject based upon a variation in the property of said signal between at least two of said plurality of time points.

Identifying the transition between a first state and a second state in a subject, for example by detecting changes in the coherence of the signal with the output signal components, allows a subject to be monitored for changes which may be related to a condition. For example, a transition in a signal emitted by a subject, at a predetermined frequency, from a coherent state to a chaotic state, may be known to be indicative of an adverse reaction (e.g. an allergic reaction). Detection of such a transition could therefore be used in identifying an unknown response, or providing additional information relating to the reaction to assist in subsequent treatment.

Said property of said signal may comprise at least one of the coherence, amplitude, frequency, and phase of said signal.

Said variation may comprise a transition from a generally coherent signal to a generally chaotic signal.

Said generally chaotic signal may be indicative of an adverse reaction in said human or animal subject.

The method may further comprise identifying a time sequence of transitions in said human or animal subject between a plurality of states.

The identification of a time sequence of transitions (e.g. a Markov chain) allows random transitions to be modelled and understood in a simple manner.

Said time sequence of transitions may be indicative of a condition in said a human or animal subject.

Prior knowledge of particular sequences which are indicative of conditions in a subject can be used to assist in the identification and treatment of such conditions.

According to a fifth aspect of the invention there is provided a computer program comprising computer readable instructions configured to cause a computer to carry out a method as described above.

According to a sixth aspect of the invention there is provided a computer readable medium carrying a computer program according to the fifth aspect of the invention.

According to a seventh aspect of the invention there is provided computer apparatus for processing a signal comprising: a memory storing processor readable instructions; and a processor arranged to read and execute instructions stored in said memory; wherein said processor readable instructions comprise instructions arranged to control the computer to carry out a method as described above.

According to an eighth aspect of the invention there is provided an apparatus for processing a signal comprising: a receiver configured to receive a plurality of components of the signal; a detector configured to detect a phase of the signal; an output buffer comprising a plurality of elements; a processor configured to populate the plurality of elements of the output buffer, each element being populated with a respective one of a plurality of output signal components, each of the plurality of output signal components being based upon one or more of the received plurality of components of the signal; and an index generator configured to generate an index for the output buffer based upon the detected phase of the signal.

It will be appreciated that features described in connection with one aspect of the invention may be combined, where appropriate, with other aspects of the invention.

BRIEF DESCRIPTION OF THE DRAWINGS

Embodiments of the invention will now be described, by way of example, with reference to the accompanying drawings in which.

DETAILED DESCRIPTION OF THE INVENTION

It has been realised that the treatment of health and wellness conditions experienced by a human or animal subject can be effected by the delivery of electrical signals to the subject. For example, conditions such as sleeplessness, high blood pressure, migraine and depression could all be treated, while weight reduction and pain relief given, by the delivery of electrical signals to the subject.

An electrical signal recorded from the subject may comprise components which originate from a number of sources, both internal and external to the subject. Components from known external sources may be removed, and remaining signal components may be regarded as being characteristic of a condition of the subject. For example, the remaining signal may be characteristic of a particular metabolic, mental or physiological state. Such recorded signals may be used to generate electrical signals to be applied to a human or animal subject as described below.

Figure 1:
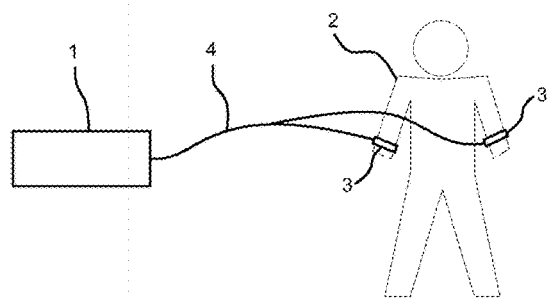
FIG. 1 illustrates a system for processing signals.

The general form of a system arranged to deliver treatments is illustrated by FIG. 1. An apparatus 1 is arranged to provide a treatment to a subject 2. A plurality of electrodes 3 are attached to the subject 2, allowing signals to be captured from, and/or delivered to the subject 2. The electrodes 3 are connected to the apparatus 1 by a cable 4. The cable 4 may be a cable which is capable of transmitting high bandwidth signals, such as, for example, a low-loss RF cable. The apparatus 1 may be configured to capture signals received from the subject 2 via the electrodes 3 and the cable 4, and/or to deliver signals to the subject 2 via the electrodes 3 and the cable 4. It will be appreciated that where appropriate a single electrode 3 may be used to deliver and/or capture signals.

The signals delivered to the subject 2 may be derived from signals which have previously been captured from the subject 2, as described in more detail below.

The electrodes 3 may take any convenient form. For example, the electrodes 3 may be conventional electrocardiogram (ECG) or electroencephalography (EEG) electrodes. Alternatively, the electrodes 3 may be finger or limb clip electrodes. The electrodes may comprise an elasticised band which is configured to be worn around a limb, for example around a wrist or ankle of the subject 2. Alternatively, electrodes may be worn around the neck of a subject like a pendant.

Generally, the electrodes 3 are transcutaneous electrodes, transmitting and receiving signals through the skin of a subject. However, in some embodiments the electrodes 3 may be subcutaneous electrodes. Such subcutaneous electrodes may, for example, at least partially, penetrate the skin of a subject and allow the transmitting and receiving of signals from within or beneath the skin of the subject. The electrodes may be, for example, similar to acupuncture needles.

The electrodes 3 are primarily configured to allow the delivery and/or detection of electrical signals to and/or from the subject. However, in an embodiment, the electrodes 3 may additionally include a plurality of sensors. For example, the electrodes 3 may include one or more sensors which monitor: skin temperature, skin conductivity, heart rate, blood oxygen level and/or blood pressure. Alternatively, such additional sensors may be provided by one or more secondary electrodes.

Figure 2:
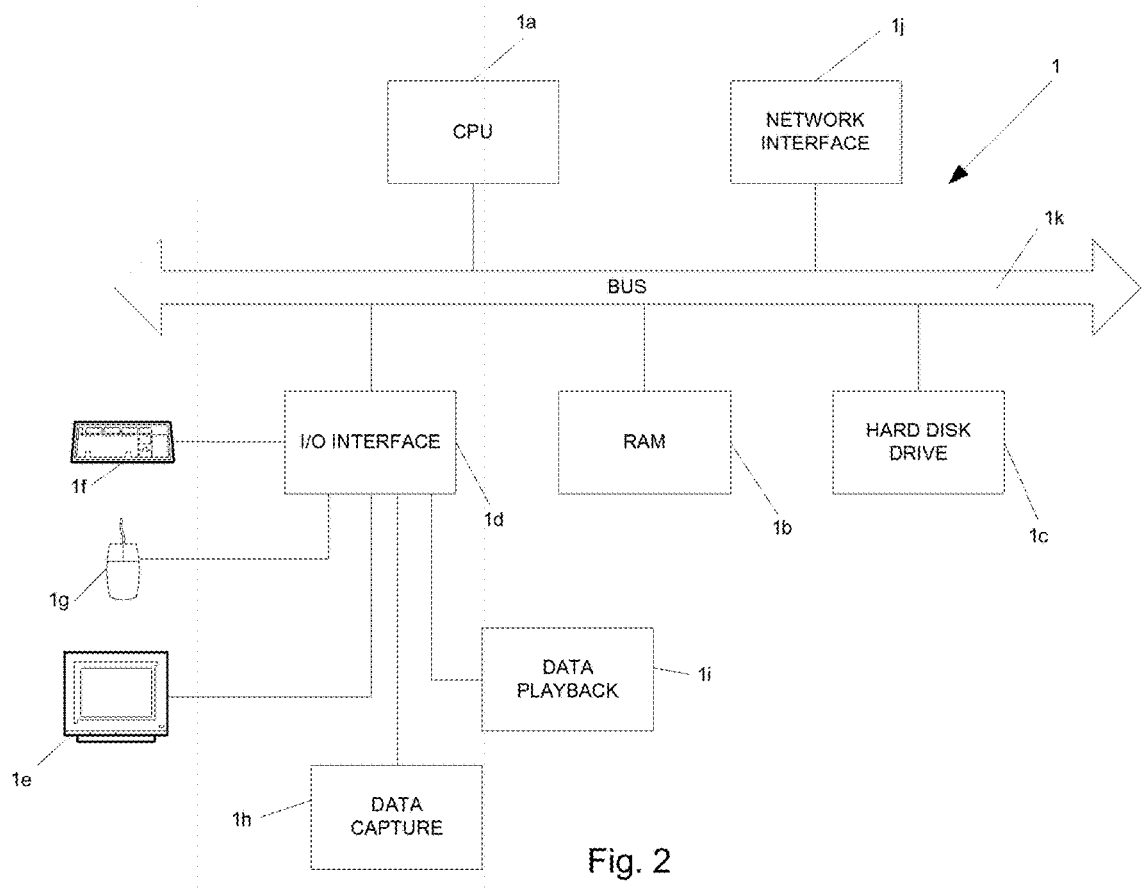
FIG. 2 illustrates an apparatus which is part of the system shown in FIG. 1.

FIG. 2 shows the apparatus 1 in more detail. It can be seen that the apparatus 1 comprises a CPU 1a which is configured to read and execute instructions stored in a volatile memory 1b which takes the form of a random access memory. The volatile memory 1b stores instructions for execution by the CPU 1a and data used by those instructions. For example, in use, signals captured from the subject 2 may be stored in the volatile memory 1b.

The apparatus 1 further comprises non-volatile storage in the form of a hard disc drive 1c. The captured signals may be stored on the hard disc drive 1c. The apparatus 1 further comprises an I/O interface 1d to which are connected peripheral devices used in connection with the apparatus 1. More particularly, a display 1e is configured so as to display output from the apparatus 1. The display 1e may, for example, display a representation of the captured signals. Additionally, the display 1e may display a representation of signals generated by processing of the captured signals. Input devices are also connected to the I/O interface 1d. Such input devices may include a keyboard 1f and a mouse 1g which allow user interaction and control of the apparatus 1. The apparatus 1 further comprises a data capture device 1h and a data playback device 1i, which are both connected to the I/O interface 1d.

It will be appreciated that the apparatus 1 may take any convenient form. For example, the apparatus may be a conventional computer connected to the capture and playback devices. It will further be appreciated that alternative or additional input and display devices may also be provided. For example, where the apparatus is a mobile telephone or tablet computer, the device's screen may serve as both display and input device (i.e. replacing the mouse and keyboard with a touch screen). Of course, such a device may additionally be provided with a separate keyboard and/or mouse should such input devices be required.

A network interface 1j allows the apparatus 1 to be connected to an appropriate computer network so as to receive and transmit data from and to other computing devices. The network interface 1j may be configured to allow the apparatus 1 to receive and transmit data via a wired or wireless network. The CPU 1a, volatile memory 1b, hard disc drive 1c, I/O interface 1d, and network interface 1j, are connected together by a bus 1k.

The data capture device 1h is configured to capture signals received from the electrodes 3, via the cable 4. The data capture device 1h may be a high-speed data capture card. For example, the data capture device 1h may be capable of sampling data at around 100 MHz (i.e. 100 million samples per second). The data capture device 1h may have a high input impedance. The data capture device 1h may convert the sampled data to digital signals, using an analogue-to-digital converter (ADC) having a resolution of, for example, 16 bits. The signals captured by the data capture device 1h may have a peak-to-peak amplitude of, for example, less than 3 V.

Signals captured by the data capture device 1h may be stored in the hard disc drive 1c, and be transferred to the hard disk drive 1c via the I/O interface 1d and the bus 1k. Alternatively, a dedicated storage device may be provided which interfaces directly with the data capture device 1h. Any such storage device should be capable of storing the digital signals which are output from the data capture device 1h. The storage device may be any suitable form or storage device (e.g. hard disk drive, solid state drive, drive array) which is capable of meeting the data storage requirements of the data capture device 1h (i.e. data capacity and data capture rate). In a further alternative embodiment, a dedicated interface may be provided which allows a storage device which is connected to the bus 1k to interface directly with the data capture device 1h, for example via a memory controller.

In addition to signals captured by the electrodes 3, the data capture device 1h may also be arranged to capture other signals, such as, for example, signals generated by other sensors relating to the properties of a physiological state of the subject (e.g. skin temperature, skin conductivity, heart rate, blood oxygen level and/or blood pressure) and other circumstantial information regarding, for example, the environment, location and/or time.

The data playback device 1*i* is configured to playback signals stored in the hard disc drive 1*c* (or other storage device) via the cable 4 and the electrodes 3 to the subject 2. By playback of a signal it is meant that the playback device generates a signal as an output which is delivered to the subject. The generated signal is based upon stored signals, as described in more detail below. The data playback device 1*i* may be a high-speed data playback card. For example, the data playback device 1*i* may be capable of outputting data at around 100 MHz (i.e. 100 million samples per second). The data playback device 1*i* may have a high output impedance. The data capture device 1*h* converts the stored data to analogue signals, using a digital-to-analogue converter (DAC) having a resolution of, for example, 16 bits. The signals output by the data playback device 1*i* may have a peak-to-peak amplitude of, for example, less than 6 V.

The apparatus 1 may take any appropriate physical form. For example, the apparatus 1 may be housed in a metal or plastic enclosure. The apparatus 1 may, for example, be powered by a connection to a mains electricity supply by a cable. The apparatus 1 may, for example, be cooled by a cooling fan.

Figure 3:
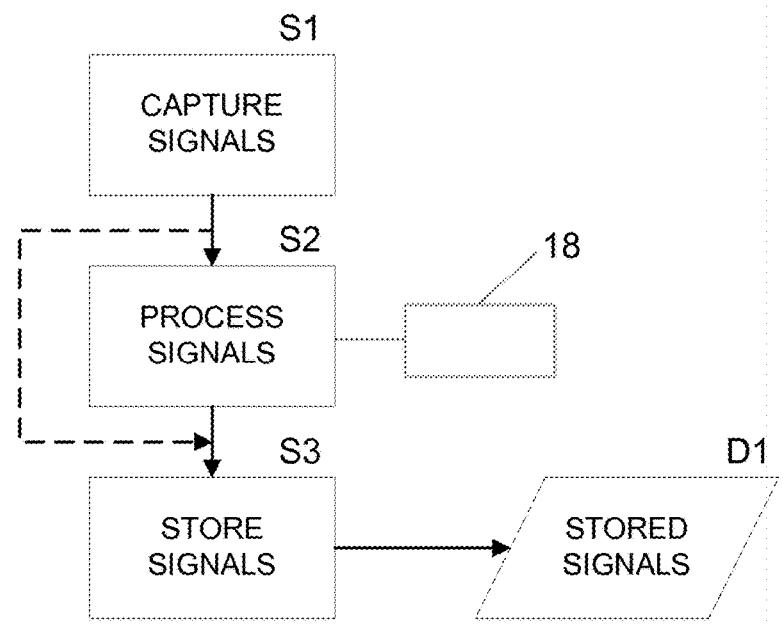
FIG. 3 illustrates a process which may be carried out by the system of FIG. 1.

A process by which signals are stored, for later use in a treatment, is illustrated in FIG. 3. At step S1 signals received at the electrodes 3 are captured by the data capture device 1*h*. Signals may be captured during a period in which the subject 2 is in a particular mental or physiological state. For example, in an embodiment signals are captured whilst the subject is exercising. Such signals (i.e. those captured during exercise) are then stored (as described in more detail below) for subsequent use in weight loss therapy. In a further example, signals captured when a subject is asleep are stored for subsequent use in therapy to treat sleeplessness.

Signals may be captured over any convenient period of time. For example, signals may be captured over a period of time which is determined by the desired effect of a treatment in which the captured signals will ultimately be used. Signals may be captured for a period of time which allows subsequent analysis to identify characteristics within the signal (for example characteristics associated with a particular condition). In an embodiment, signals may be captured for a period of, for example, 5 minutes. In alternative embodiments, different capture periods may be used.

The captured and digitised signals are then processed at step S2. The processing may include techniques such as, for example, sampling, amplification, noise reduction, splicing, frequency filtering, and looping. For example noise reduction may comprise processing the captured signals to remove components of the signals which originate from sources which are not of interest. Such components may be regarded as noise.

For example, signals which originate from mains electricity distribution networks (e.g. at 50/60 Hz) may be present in the captured signals and may be regarded as noise. Such signals may, for example, be removed by frequency filtering. That is, any signals which occur at a frequency which is known to be the local mains electricity distribution frequency may be removed. Such filtering may be known as band-stop filtering. Frequency filtering may be applied to other sources of unwanted noise as appropriate. Frequency filtering may further comprise other frequency based techniques, such as, for example, one or more of high-pass, low-pass or band-pass filtering. Such filtering may be carried out, for example, by software defined radio.

Further sources of noise may be pulses which originate from bodily organs. For example, heartbeat pulses (that is, pulses which are caused by the heartbeat of the subject 2), may contribute an unwanted signal component. Such heartbeat pulses may be removed from the captured signals by comparing the captured signals with a separately captured signal which corresponds to the heartbeat of the subject 2. That is, a background recording (the separately captured signal) may be effectively subtracted from the captured signal, allowing a component of the captured signal which corresponds to the heartbeat pulses to be removed. Alternatively, a known characteristic of a heartbeat pulse may be used to identify and remove a heartbeat pulse. For example, heartbeat pulses may be known to have an approximately similar characteristic pulse shape. Any pulse which matches the characteristic pulse shape to predetermined extent may be classified as a heartbeat pulse and removed from the captured signal accordingly.

It will be appreciated that other unwanted signals may be removed in a similar way to those described above, for example by frequency filtering, by background recording and subtraction, or by feature identification and removal. Other noise reduction techniques may also be used.

For example, any form of repeating patterns may be detected and subtracted from a captured signal. Such repeating patterns may be captured in measurements taken from a subject, or from a local environment in which a subject is located, and subsequently subtracted from the captured signal. Furthermore, elements of a repeating pattern may be detected in a captured signal and modelled, so as to generate a modelled signal which can be subtracted from the captured signal. Such detection and modelling allows disturbances such as repeating background noise to be eliminated from a captured signal.

Captured signals may be further processed to remove unwanted signal components. For example, captured signals can be processed by genetic search and categorisation algorithms in order to identify known patterns within the captured signals. Once identified, the known patterns can be either discarded (e.g. by subtraction from the captured signal), enhanced (e.g. by amplification), or isolated (e.g. by removal of all other signals) for further use either alone or in combination with other signals or signal components.

Further processing of captured signals may be carried out by artificial neural networks, for example to analyse signal frequencies, signal phases, signal amplitudes and signal patterns. Fourier, sine and cosine transforms may also be used to convert signals between time and frequency domains, for processing.

Noise reduction may be accomplished by frequency and/or phase locking to captured signals in order to achieve an output which is aligned with (in terms of frequency or phase) with a particular signal.

Donor signals may be extracted from captured signals so as to be used in subsequent playback. That is, donor signals are components of a signal captured from a subject which are extracted or isolated from the captured signal and are subsequently included within a signal which is played back to a subject. Suitable donor signals may be selected based upon a characteristic of the donor subject, or a group of donor subjects. Such donor signals may be extracted from the captured signals by techniques described above (e.g. genetic search and categorisation). Further, donor signals may be identified by auto- and cross-correlation techniques. Fractal processing algorithms may also be used to distinguish between chaotic and/or complex events and random noise. In an embodiment, the fractal processing described above is carried out in accordance with the Grassberger-Procaccia algorithm or variants thereof.

The processing of step S2 may be carried out by dedicated hardware or by software routines. For example, the processing of step S2 may be carried out by the data capture device 1h, or within the CPU 1a.

The processed signals are then stored at step S3, as stored signals D1. As described above with reference to FIG. 2, the stored signals D1 may be stored within any suitable storage device, such as, for example the hard disk drive 1c.

In an embodiment, the signals captured by the data capture device 1h at step S1 may be stored at step S3 without being processed at step S2. This process is shown by a dashed line in FIG. 3.

Figure 4:
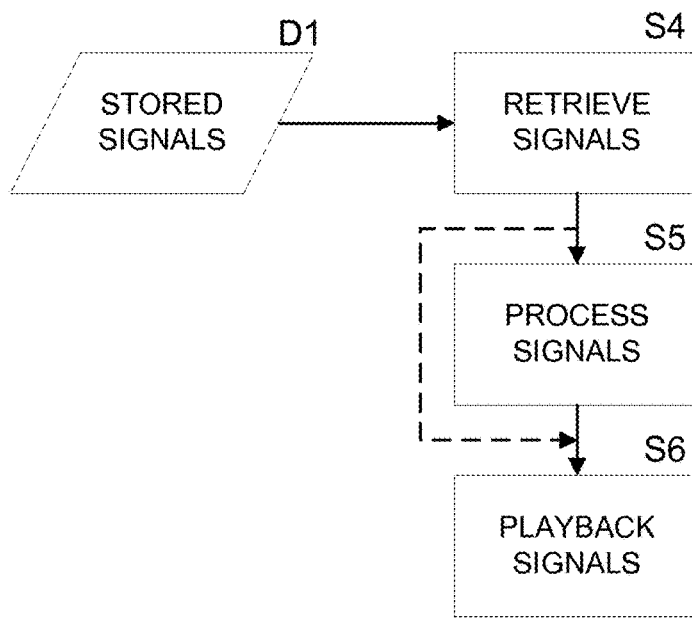
FIG. 4 illustrates a further process which may be carried out by the system of FIG. 1.

A process by which stored signals are retrieved for use in a treatment of a subject, is illustrated in FIG. 4. At step S4 the stored signals D1 are retrieved from a storage location. The retrieved signals are then processed at step S5 such that the signals are in a form which can be applied to the subject. For example the signals may be processed to remove contributions which original from sources which are not of interest (as described above). Other processing techniques may be used as appropriate.

The processing of step S5 may be carried out by dedicated hardware or by software routines. For example, the processing of step S5 may be carried out by the data playback device 1i, or within the CPU 1a.

At step S6 the processed signals are then played back to the subject 2 by the data playback device 1i through the electrodes 3, which are attached to the subject 2, as described above with reference to FIG. 1.

In an embodiment, the retrieved signals may be played back at step S6 without being processed at step S5. This process is shown by a dashed line in FIG. 4.

The signals may be played back to the subject 2 at a time when a desired effect is required to be induced in the subject 2. For example, when there are differences between a desired state (e.g. sleep) and a present state (e.g. sleeplessness) a signal which was captured when the subject was in the desired state (e.g. sleep) is played-back to the subject. The signals played-back to the subject may either be in the form in which the signal was captured, or having been processed in some way, in order to induce the desired state. The signals captured during the desired state contain components which are characteristic of that state. For example, the signals may contain components which are characteristic of a slow metabolic rate during sleep. On the other hand, the subject 2, when in a sleepless state, may have a higher metabolic rate than that observed during sleep. The playing-back of a signal having components which are characteristic of a slow metabolic rate may induce sleep.

A high-bandwidth signal is considered to be more effective at inducing a desired state, and is therefore preferred to be used (as compared to a low-bandwidth signal). In order to generate a high-bandwidth signal during playback, a high-bandwidth signal is also captured, so as to capture signals from a variety of potential biological sources. For example, signals may be captured at cellular and cell structural levels, as well as from the central and autonomous nervous systems. It is understood that microtubules (a common building block of almost all biological human and animal cells) have typical RF resonances between around 12 kHz and 8 MHz. Literature which discusses such measurements on microtubules, and other electromagnetic cellular interactions can be found, for example in: 'Biosensors and Bioelectronics Volume 47, September 2013, Pages 141-148, Atomic water channel controlling remarkable properties of a single brain microtubule: Correlating single protein to its supramolecular assembly: Satyajit Sahua, Subrata Ghosha, Batu Ghoshc, Krishna Aswanid, Kazuto Hiratab, Daisuke Fujitaa, Anirban Bandyopadhyaya'; 'Journal of Physics: Conference Volume 3-29 Conference 1, 2011, Electric Field generated by longitudinal axial microtubule vibration modes with high spatial resolution microtubule model: M Cifra, D Havelka, M A Deriu'; 'Bioelectrochemistry Volume 63 2004 Pages 321-326 Excitations of vibrations in microtubules in living cells Pokorny J', and 'Progress Biophysical Molecular Biology. 2011 May Pages 223-246, Electromagnetic cellular interactions. Cifra M, Fields J Z, Farhadi A'.

In order to capture phase detail at these high frequencies, an even higher sampling rate may be required. For example, in order to capture phase detail at 8 MHz, without using high order analogue anti-alias filtering, a sampling rate such as 120 million samples per second can be used. Such a system may use an RF system having a bandwidth capability of, for example, DC-60 MHz. Such a capability allows the RF system to directly capture and record the sub-cellular oscillations, and to replay the captured signals in order to induce and/or reproduce a similar state at the sub-cellular level.

It will be appreciated that such a system is not limited to use capturing and replaying signals from/to microtubules. High-bandwidth signals may be used to capture and induce activity within other cellular components such as biological ATP powered molecular motors, mitochondria and cell regulation in centrosomes.

Where a system is intended for use instead with signals which originate from biological systems such as, for example, ECG, EEG or a subject's nervous system, lower sampling rates (such as, for example, DC-1 MHz) could be used.

The signals played back to the subject 2 when a desired effect is required to be induced in the subject may be played repeatedly. For example, the signals maybe looped such that a continuous signal is played back to the subject which comprises a plurality of signal components, each of which is similar or identical to one another, but offset with respect to one another by a period of time which is equal to the duration of each of the plurality of components.

During playback, further signals may also be captured from the subject 2. For example, in one embodiment a first electrode and cable are configured to deliver a played back signal to the subject 2 while a second electrode and cable are configured to monitor a characteristic of the subject 2. The monitored characteristic may, for example, be the heart rate of the subject 2. The monitored characteristic may be monitored by a computer routine running on the CPU 1a. Alternatively the monitored characteristic may be monitored by the subject 2, or by a skilled operator who is administering treatment. Such monitoring may be used to control the delivery of a played-back signal.

The monitored characteristic may be used to control the delivery of the played-back signals. For example, in an embodiment, a characteristic which is indicative of sleep (e.g. heart rate) may be monitored. When the monitored characteristic satisfies a predetermined criterion (e.g. falls below a predetermined threshold value, indicating that the subject 2 is asleep), the playback may cease. It will be appreciated that such control may be based upon characteristics of the individual subject (e.g. a measured sleeping heart rate) or may be based upon average characteristics of a population (e.g. a predetermined change in heart rate).

Sleep patterns may also be monitored and/or influenced using EEG data, and delta, theta, alpha, beta and gamma brainwaves in the frequency range 4-42 Hz. Such signals may be captured and recorded from a subject during sleep, and replayed to the subject at a later time. For example, signals may be captured using head mounted electrodes, and subsequently replayed to a subject using simpler body electrodes.

The monitored characteristic may also be used to control the delivery of the played-back signals in other ways. In an embodiment, a characteristic of the subject may be monitored, and the playback of signals adjusted in accordance with the monitored characteristic. For example, a plurality of signals (e.g. ECG, EEG or microtubule resonant signals) may be available for playback, and an appropriate signal selected from the plurality of available signals based upon the monitored characteristic. A new signal may be selected for playback at periodic intervals, or when the duration of a selected signal expires. The new signal may be the same as the previously selected signal, or a different one of the plurality of available signals depending on the monitored characteristic. The signals may be selected, for example, in accordance with a predetermined playback sequence.

It will be appreciated that in some embodiments signals may be processed during the capture and storage process (e.g. at step S2, FIG. 3), during the retrieval and playback process (e.g. at step S5, FIG. 4), during both the capture and storage process and the retrieval and playback process, or not at all. Alternatively, stored signals may be processed during processing which is carried out for the sole purpose of processing the stored signals, rather than as part of a capture or storage process. For example, stored signals may be retrieved, processed and re-stored for later use in playback. This may be particularly beneficial where the processing requires significant processing power, which may not be available at the point of capture or playback (for example where portable capture/playback devices are used, as described in more detail below).

As referred to above, the signals delivered to the subject 2 may be derived from signals which have previously been captured from the subject 2. However, in addition, signals delivered to the subject may be derived from other sources. For example, the signals delivered to the subject 2 may be derived from signals which have previously been captured from another subject. In particular, the signals delivered to the subject 2 may be derived from signals which have previously been captured from another subject who shares one or more characteristics or desired characteristics with the subject 2. For example, a signal captured from a subject who has recovered from a condition may be used in the treatment of a subject who has that condition.

It will be appreciated that captured signals may be stored and/or processed by remote servers, for example cloud-based computing facilities. Such remote storage and processing allows a large amount of data to be stored and processed, and for captured signals from a large number of subjects to be processed by a single computing resource. Further, signals for playback to a subject may be derived from the large number of signals which are processed and/or stored by a remote server, allowing donor signals to be extracted from a large number of captured signals originating from one or more subjects.

Signals which are delivered to a subject during playback, and which are derived from signals previously captured from the subject (or indeed another subject) may be processed in some beneficial way prior to playback. For example, captured signals may be shifted in amplitude or frequency or synchronised with a local oscillation source relevant to the subject being treated. A local oscillation source may, for example, be dependent upon the subject's location on the Earth and the time of day (e.g. diurnal). Alternatively, or in addition, a local oscillation source may be related to the subject's local environment. In a further alternative, a local oscillation source may be generated by the subject (e.g. heartbeat, brainwaves, chaotic cell oscillations).

A signal delivered to a subject may also be based upon a captured signal which is re-arranged, with various signal components being combined in a particular way so as to produce an output signal which has a particular characteristic. For example, signal components may be looped, or played concurrently so as to stimulate a particular effect.

In a further alternative, the signals delivered to the subject 2 may be synthesised signals which are synthesised for the purpose of the treatment of a particular condition. Further, it will be appreciated that a signal delivered to a subject may comprise a combination of signals from different sources. For example, a signal delivered to a subject may comprise a component signal which is derived from a signal previously captured from the subject 2, and a second component signal which is a synthesised signal.

Synthesised signals may be modelled upon signals which are captured from a subject. For example, characteristics of signals which are captured from a subject may be modelled, and a synthesised signal reconstructed based upon those modelled characteristics. Signal characteristics which may be subject to such reconstruction could be, for example, phase, frequency or any other waveform pattern. A synthesised waveform could be adjusted so as to modify a particular characteristic, while others remain constant. For example, the amplitude of a particular feature (e.g. having a characteristic frequency) of a synthesised signal could be enhanced, while other features remain constant.

Synthesised signals may also be re-arranged, with various synthesised signal segments being combined in a particular order so as to produce an output signal which has a particular characteristic.

The processing required to synthesise a signal for playing-back to a subject may be carried out by the CPU 1*a* within the apparatus 1. The processing required to synthesise a signal for playing-back to a subject may be carried out by the CPU 1*a* within the apparatus 1 in real-time (i.e. as the signal is required to be played-back) or in advance of being required. Alternatively, the processing required to synthesise a signal for playing-back to a subject may be carried out by a processor remote from the apparatus. Any such synthesised signal may be transmitted to the apparatus 1, for storage prior to possible subsequent use, or for immediate playback (i.e. the synthesised signal is streamed to the apparatus 1 in real-time), via a network to which the apparatus 1 is connected.

In an embodiment, signals captured from the subject 2 may be monitored. For example, a computer routine running on the apparatus 1 maybe be configured to identify predetermined characteristics within the captured signals, and to take appropriate action in dependence upon the identification of those predetermined characteristics. For example, a captured signal may be stored only when a predetermined criterion is met. Alternatively, or in addition, a captured signal may be processed only when a predetermined criterion is met. The predetermined criterion may be any predetermined physiological, mental or metabolic state of the subject 2 (e.g. sleep). In this example, if a captured signal is required when the subject 2 is asleep, any signals captured when the subject 2 is not asleep would not be useful, and as such do not require storage.

Alternatively, captured and stored signals may be subsequently analysed and discarded if they are not considered to be of any further use. Captured signals are not therefore required to be stored.

Alternatively, signals captured from the subject 2 may be monitored by the subject themselves or by a skilled operator who is present with the subject 2, or who may be remotely connected via a network. The apparatus 1 may be arranged to provide audio or visual feedback to the subject 2 (or to a skilled operator) based upon the captured signals. The skilled operator may assist the subject 2 with the recording process. Similarly, a skilled operator may assist the subject 2 with the playback process.

Signal processing techniques used to process signals of the type described herein are now discussed. A loosely coupled oscillator may, for example, be used to identify and/or extract donor signals, or to generate an output which is indicative of a state of an input signal. A loosely coupled oscillator is a form of oscillator which operates within a frequency band, rather than at a single resonant frequency. Further, a loosely coupled oscillator operates with a fixed phase relationship with a periodic input which is not necessarily a sinusoid. For example, the loosely coupled oscillator may be synchronised with a periodic (but not necessarily sinusoidal) waveform, and may have an output which is synchronised with the input. However, rather than having an output which is a sinusoid (as would be the case with an LC resonant circuit), the output of the loosely coupled oscillator is a series of repeating signal components, which are controlled by the input.

For example, the output of the loosely coupled oscillator may be a signal component based upon a property of the input to the loosely coupled oscillator. Moreover, the loosely coupled oscillator may take the form of a rotating oscillator, which rotates through a plurality of signal components based upon a phase relationship between the current input and the current output. Each of the plurality of signal components corresponds to a detected input signal component. The phase of the detected signal is monitored by a phase detector having a fixed length (e.g. a time period based upon the centre frequency of the frequency band in which the loosely coupled oscillator operates). The detected phase is then used to cycle through the plurality of signal components. In an embodiment each of the plurality of signal components is stored in an output buffer (e.g. a circular buffer), and the detected phase used to determine a rotating vector which operates as an index for the circular buffer. The rotating vector is incremented by the output of the phase detector.

The plurality of signal components (i.e. the contents of the circular buffer) are derived from detected signals by applying a function (either linear or non-linear) to inputs. For example, signal components may be generated by applying a function such as an averaging filter or integrator to the inputs, which are detected signals. The contents of the circular buffer may also be used as an input to a function used in deriving further contents of the circular buffer.

The circular buffer may thus be populated with signal components which are derived from signals captured from a subject. For example, a repeating signal captured from a subject allows the circular buffer to be populated with a copy of that signal. In use, the loosely coupled oscillator generates an output based upon the copy of the signal. The phase detector then monitors the phase of the input signal and controls the output of the loosely coupled oscillator to be synchronised with the input signal. Any deviation of the input signal (e.g. in amplitude, frequency or waveform shape) causes the output of the phase detector to change. Any such change which is also gradual can be used to tune the output of the loosely coupled oscillator (e.g. to speed up or slow down the rotation of the oscillator), so as to maintain the phase relationship between the input signal and the output. However, where a change in the input signal (as detected by the phase detector) is abrupt, for example if the input signal switches to a complex or chaotic signal, the output of the loosely coupled oscillator is not able to track the input signal. Such a loss of coherence between the input signal and the output buffer causes the output buffer to be gradually updated with random noise, reducing the amplitude of any copy of the earlier coherent input signal.

Figure 5:
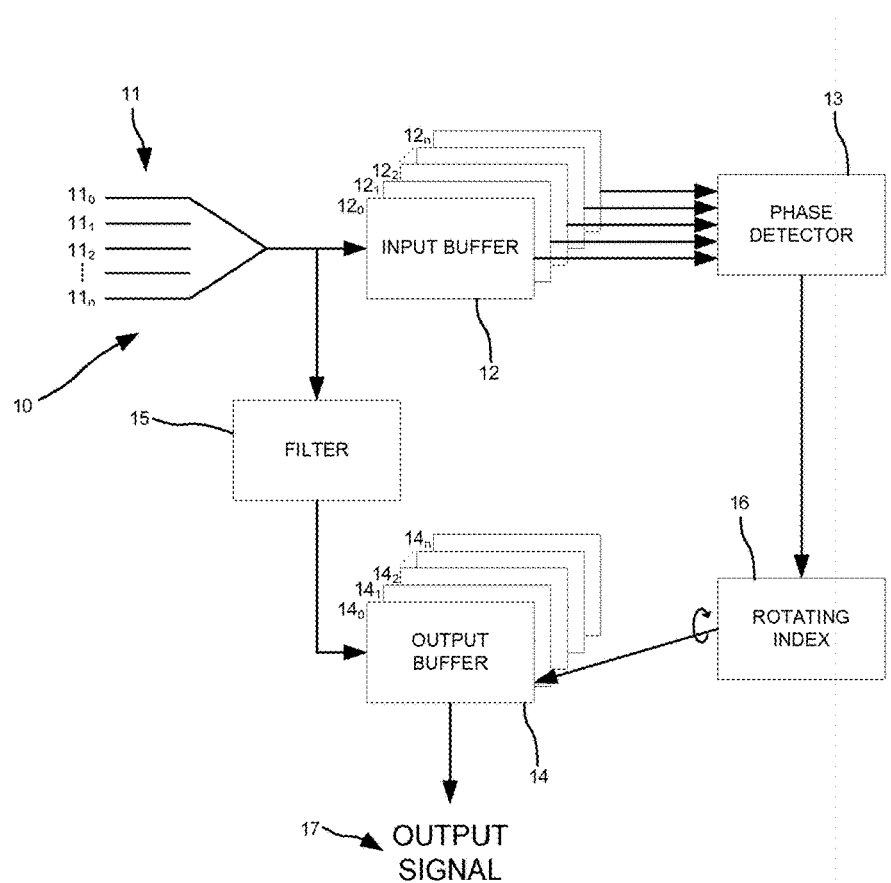
FIG. 5 illustrates a system for processing signals.

Having described the general principles of a loosely coupled oscillator, a specific embodiment of such an oscillator is now described with reference to FIG. 5. A loosely coupled oscillator 10 receives an input signal 11 from a capture device (not shown). The input signal 11 is a signal captured from a subject and comprises a plurality of input signal components $11_0$, $11_1$, $11_2$, etc. Each of the input signal components $11_{0-n}$ corresponds to a sample captured by the capture device. For example, each of the input signal components may be a 16-bit signed value output by an ADC within the capture device which represents the amplitude of a waveform at a respective point in time. Alternatively, the input signal components may be retrieved from a signal which has been captured and is stored in a storage device.

The input signal 11 is passed to an input buffer 12. The input buffer 12 operates as a delay line, with the contents of the buffer gradually proceeding along the buffer i.e. the buffer acts in a similar manner to a shift register. The input buffer 12 has a plurality of buffer locations $12_0$, $12_1$, $12_2$, . . . $12_n$. On receiving a first input signal component $11_0$, the first input signal component $11_0$ is copied to the first buffer location $12_0$. On receiving a second input signal component $11_1$, the second input signal component $11_1$ is copied to the first buffer location $12_0$, and the previous contents of the first buffer location $12_0$ (i.e. the first input signal component $11_0$) is copied to the second buffer location $12_1$, and so on. In this way, the input buffer 12 is populated with the input signal 11.

The input buffer 12 is monitored by a phase detector 13. The phase detector 13 monitors the phase of the input buffer 12, for example by comparing the values stored in each of the input buffer locations $12_{0-n}$. The phase detector 13 generates an output which is indicative of the current phase of the input signal 11, based upon the values stored in the input buffer 12.

The number of input buffer locations, n, is any convenient predetermined number (e.g. 100). The number of input buffer locations may be selected to allow the phase of the input signal 11 to be conveniently detected. For example, where the input signal 11 comprises a periodic waveform, the number of input buffer locations may be selected so as to allow the input buffer 12 to contain at least one half waveform of the periodic waveform. The number of input buffer locations may be increased (e.g. so as to allow the input buffer 12 to contain a whole waveform of the periodic waveform) to allow more accurate phase detection to be carried out.

The loosely coupled oscillator 10 further comprises an output buffer 14. The output buffer 14 comprises a plurality of output buffer locations $14_0$, $14_1$, $14_2$, . . . $14_n$ which are linked so as to form a circular buffer. The input buffer 12 and output buffer 14 may have an equal predetermined number, n, of buffer locations Position $14_1$ of the output buffer 14 follows position $14_0$, position $14_2$ follows position $14_1$, and so on until position $14_n$ follows position $14_{n-1}$ and position $14_0$ follows position $14_n$. The output buffer locations $14_{0-n}$ are populated by signals which are derived by passing the input signal 11 through a filter 15. The filter 15 may, for example, have a non-linear function, such as an integrator or an averaging filter. This is described in more detail below.

The loosely coupled oscillator 10 further comprises a rotating index 16. The rotating index 16 points to a location in the output buffer 14, and is advanced at regular intervals such that the rotating index 16 cycles through each of the output buffer locations $14_{0-n}$. An output signal 17 is generated by, at each of a plurality of time points, selecting an output from the output buffer indicated by the rotating index 16. In use, the output of the phase detector 13 causes the rotating index 16 to advance so as to generate an output signal 17 which is in phase with the input signal 11. The rotating index 16 has a nominal rate at which it advances, which can be increased or decreased within a band by the phase signal received from the phase detector 13. The output buffer generates an output signal 17, which is an approximation of the input signal 11. The input and output signals 11, 17 are maintained at a similar frequency and phase by the operation of the phase detector 13 and the rotating index 16.

The number of output buffer locations (n), and the (nominal) rate at which the rotating index 16 is advanced determine the nominal frequency of the loosely coupled oscillator 10. The band within which the rate of advance of the rotating index 16 can be varied determines the frequency band within which the loosely coupled oscillator can operate, and thus the frequency band within which any input signal 11 can be followed and copied to the output buffer 14.

In order to increase or decrease the frequency at which the loosely coupled oscillator 10 operates, the rotating index 16 is able to advance at a fractional rate. That is, the rotating index 16 continues to be updated at the nominal rate, however, the output of the rotating index 16 is able to skip over output buffer locations (in order to match an increased input signal frequency), or to repeat output buffer locations (in order to match a reduced input signal frequency). For example, for a loosely coupled oscillator having a nominal output frequency of 1 MHz, and a buffer length (n) of 100, in order to match an input signal having a frequency of 0.99 MHz, for every full cycle of the output buffer, approximately one buffer location should be repeated (i.e. making each cycle of the buffer contain on average 101 samples, rather than 100 samples). On the other hand, for a loosely coupled oscillator having a nominal output frequency of 1 MHz, and a buffer length (n) of 100, in order to match an input signal having a frequency of 1.01 MHz, for every full cycle of the output buffer, approximately one buffer location should be skipped (i.e. making each cycle of the buffer contain on average 99 samples, rather than 100 samples).

It will be appreciated that a larger or smaller number of buffer locations can be skipped or repeated as required in order to cause a desired output frequency adjustment. Further, any such adjustment does not need to be carried out on every buffer cycle. For example, to cause a frequency increase of around 0.5% one buffer location can be skipped every two full cycles (i.e. one skip every 200 output buffer locations, assuming an output buffer length of 100). Similarly, to cause a frequency decrease of around 0.5% one buffer location can be repeated every two full cycles (i.e. one repeat every 200 output buffer locations, assuming an output buffer length of 100).

Further still, the buffer locations which are skipped or repeated may be rotated, in order to reduce or prevent output signal distortion. For example, if 1 buffer location in every 101 samples is required to be skipped, on a first cycle of the output buffer this may be buffer location $14_0$, on a second cycle of the output buffer this may be buffer location $14_1$ and so on.

The phase detector 13 described above may be a phase discriminator, having a single input from the input buffer 12. Alternatively, the phase detector 13 may have an input directly from the input signal 11. The phase detector 12 may also have an input from the output buffer 14 and/or the output signal 17. Such a phase detector may also be known as a phase comparator. Such a phase detector or phase comparator may be arranged to generate an output which is indicative of the difference in phase between the input buffer 12 (or input signal 11) and the output buffer 14 (or output signal 17).

In operation the contents of the output buffer 14 (and thus the output signal 17) is continually updated based upon the input signal 11. For example, each of the output buffer locations $14_{0-n}$ contains a value which represents the amplitude of the input signal at a respective point in its oscillation. The filter 15 may, for example, have a function which generates a value based upon the previous several input signal 11 values which correspond to a particular output buffer location $14_{0-n}$. Where the input signal 11 comprises a periodic waveform, and the sampling rate of the input signal 11 is appropriately selected, each time the periodic waveform repeats each of the output buffer locations $14_{0-n}$ is updated to take into account the most recent occurrence of the periodic waveform within the input signal 11. However, rather than being a direct copy of the most recent occurrence of the periodic waveform, the output buffer 14 retains information relating to previous occurrences of the periodic waveforms within the input signal 11.

For example, the output buffer 14 may contain an average signal based upon the input signal 11. The average signal may take the form of a weighted average. Taking as an example an average over three occurrences of the periodic waveform (where a first occurrence occurs most recently and a third occurrence occurs least recently for ease of reference), each output buffer location $14_{0-n}$ may be associated with a particular sample point of the periodic waveform and may contain a value which consists of 50% of a respective sample value of the first occurrence of the periodic waveform, 25% of the respective sample value of the second occurrence of the periodic waveform and, 12.5% of the respective sample value of the third occurrence of the periodic waveform. The output buffer 14 thus contains a waveform which is a weighted average of the previous three occurrences of the periodic waveform.

In such a loosely coupled oscillator, after a single cycle of the periodic waveform, the output buffer 14 will contain a low level copy (i.e. a reduced amplitude copy) of the periodic waveform included in the input signal 11. After a second cycle of the periodic waveform, the output buffer will contain a copy which is approximately 75% of the amplitude of the periodic waveform. After a third cycle of the periodic waveform, the output buffer will contain a copy which is approximately 87.5% of the amplitude of the periodic waveform, and so on.

It will be appreciated that, in general terms an average may be taken over some m occurrences of the periodic waveform and that occurrences may be weighted in any suitable way—the weighting factors need not form a geometric progression.

The loosely coupled oscillator 10 may be implemented by software routines running on the processor 1a.

Figure 6:
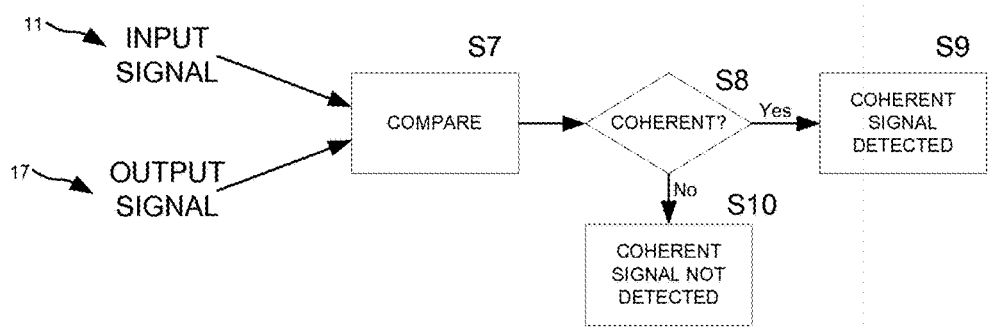
FIG. 6 illustrates a process which may be carried in accordance with the system of FIG. 5.

The output signal 17 can be used to generate an indicator that the output of the loosely coupled oscillator 10 does not represent the input signal 11. A process by which the output signal 17 generated by the loosely coupled oscillator is used to generate such an indicator is illustrated in FIG. 6. At step S7 the input signal 11 and the output signal 17 are compared. The comparison generates a difference signal which is indicative of the degree of coherence between the input signal and the output signal 17. At step S8 the difference signal is compared to a predetermined threshold. If the difference signal is below the threshold, then the current input signal is classified as coherent (i.e. the input signal 11 is coherent with the time averaged version of the input signal—the output signal 17), and processing passes to step S9. At step S9 further processing is carried out which is based upon the form of the output signal 17. If the difference signal exceeds a threshold, then the current input signal is classified as incoherent and processing passes to step S10. At step S10 further processing is carried out based upon the lack of coherence between the input signal 11 and the output signal 17. For example the further processing at step S10 may comprise alerting a subject, a skilled operator, or a software routine of a change of state of the subject.

The processing at step S8 may further include a comparison of a plurality of difference signals corresponding to a respective plurality of input and output signal components. For example, a single difference value exceeding a threshold may be considered to be permissible, while several successive difference values may be indicative of incoherence. Alternatively, or in addition, the processing at step S8 may compute an integral or average of the difference values across a predetermined time period (e.g. preceding 10 samples).

The loosely coupled oscillator 10, can be used, as described above, to analyse signals captured from a subject. Further, the output of the loosely coupled oscillator 10 (i.e. the output signal 17) may be stored for subsequent analysis. The output of the phase detector 13 may be stored for subsequent analysis.

This form of signal processing allows different biological signalling waveforms to be interpreted and categorised. For example, signals which are captured from a subject may contain various periodic features, with frequencies which range from DC to 100 MHz. Such signals may contain several signal components at a particular frequency, or within a particular frequency band, which are in some way related. For example, the amplitude, frequency or waveform shape of a signal in a particular frequency band may gradually change in time. Such a signal may also undergo a transition from a coherent waveform to a complex or chaotic waveform, either spontaneously, or in response to an external stimulus (e.g. a sound). Such a transition can be detected by the processing described with reference to FIG. 6, to allow a treatment program to be modified or completed.

In embodiments of the invention the detection of such a transition (from a coherent waveform to a complex or chaotic waveform, or vice versa) is used to control an apparatus which is capturing or playing back data from or to a subject. Alternatively, such a transition maybe used to identify a characteristic response. For example, a detection apparatus worn about or connected to the body may continuously monitor a signal, properties of which are indicative of a response, such as an allergic reaction. If the allergic reaction is triggered (albeit at a low level) the detection apparatus is able to detect a transition from a signal waveform which is indicative of a normal state (e.g. coherent) to one which is indicative of an allergic reaction (e.g. chaotic). Such a detection apparatus could be configured to provide an early warning of an allergic reaction. Similar detection apparatus could be configured to monitor a subject during an exercise program for particular indicators of physiological stress (e.g. to prevent injury, or to enhance a desired training effect). A detection apparatus could also be configured to provide bio-feedback based upon the monitoring of a subject. For example, the bio-feedback could be displayed upon the screen of a smart-phone, or on a head-up-display worn by the subject.

Further, such a detection apparatus could be configured to monitor a subject while performing everyday tasks at a plurality of frequencies, generating a signature of that subject when performing everyday tasks. Such a signature could subsequently be used in a treatment program to identify particular physiological or metabolic states, which may only be identified by reference to an individual subject. For example, each subject may emit signals at a set of frequencies with is unique to them within a population.

Those emitted signals may be generated as a result of communication between cellular or sub-cellular components within any biological (human, animal, plant) system. Cells may themselves operate as biological loosely coupled oscillators at the frequencies of the low amplitude electromagnetic signals, and are synchronised by the signals. This synchronisation between various cells can allow signals to be effectively relayed around a larger system or body, the biological loosely coupled oscillators acting as signal repeaters.

Alternatively, the cellular or sub-cellular components may be coupled by other signalling mechanisms, for example mechanical means (e.g. acoustic or ultrasonic). Cellular proteins may act as charge carriers, allowing electromagnetic signals to be carried or generated by such proteins. Further, signals may also be generated or received by proteins which exhibit piezoelectric effects, allowing energy to be converted between electrical and mechanical forms.

Biological loosely coupled oscillators do not necessarily rely on operating at a single frequency, but instead are able to synchronise with incoming waveforms across a wide band of frequencies. Loosely coupled oscillators according to embodiments of the invention may be arranged in a similar fashion (i.e. able to operate across a wide frequency range). In fact, a biological system may comprise a plurality of loosely coupled oscillators each operating in different frequency bands, allowing parallel transmission of signals between networks of the loosely coupled oscillators. Embodiments of the invention may be arranged in a similar fashion (i.e. having a plurality of loosely coupled oscillators each able to operate at a different frequency band).

In biological systems, cellular or sub-cellular components operating as loosely coupled oscillators may be controlled by biological processes, and may switch between coherent and complex signal waveforms in response to those biological processes. A biological loosely coupled oscillator may operate simultaneously as a transmitter (having an output) and a receiver (having an input), and provide a mechanism for the transmission of signals within the biological system.

Loosely coupled oscillators according to embodiments of the invention (e.g. loosely coupled rotating oscillator) may be arranged to respond to biological signals in a similar fashion to loosely coupled oscillators within a biological system. Loosely coupled oscillators according to embodiments of the invention allow phase changes and transitions between coherent and complex or chaotic signals to be detected, modelled and processed. The loosely coupled oscillators described above are thus able to synchronise with an input signal, and to generate an output which is either based upon the (coherent) input signal, or indicative that the input signal is complex or chaotic.

The signal-to-noise ratio of a captured signal may be improved by introducing a stimulus while the signal is being captured from a subject. For example, certain signals within a human or animal subject may increase in amplitude in response to increased external noise sources (e.g. where those signals are involved in communication or signalling within a subject). Therefore, by introducing a noise source having a known characteristic (e.g. white noise having a substantially constant power spectral density within a particular frequency band), the amplitude of signals generated within the body may be increased, in order to compensate for the increased noise level. This increase allows a greater signal-to-noise ratio (with respect to external noise sources) to be achieved. The external noise source may be the source of energy for the oscillators in the body.

Further, a stimulus signal may perturb a signal source within a subject. For example a stimulus signal comprising a frequency sweep may stimulate naturally occurring loosely coupled oscillators within a subject. Capturing signals as the frequency sweep is applied allows the oscillation of such oscillators to be observed. For example, a naturally occurring loosely coupled oscillator may oscillate in response to the perturbation of the frequency sweep after a delay period.

Signals captured from a subject by techniques described above can be processed to identify key frequencies at which information is carried, for example by the application of a Fourier transform (e.g. DFT, FFT). Such information allows a loosely coupled oscillator having a frequency at or around one of the identified frequencies to be used to further analyse the captured signals. It will be appreciated that a plurality of loosely coupled oscillators, each having a different frequency band, may be used to allow a respective plurality of key frequencies to be observed for the presence of coherent signals, as described above.

Further, a captured signal may be processed in this way (i.e. with key frequencies identified), so as to allow efficient processing and storage. A broadband capture and storage approach (i.e. capturing and storing signals across a broad range of frequencies) will generate a large volume of data for storage. However, if captured broadband signals are channelised (i.e. split into frequency channels) and only those channels corresponding to key frequencies stored, significant reductions in data storage requirements can be brought about. Similarly, the use of decimators on the extracted channels allows a further reduction in the data storage requirements (by reducing the effective sampling rate of the captured signals).

Alternatively, or in addition to the detection of transitions between coherent and chaotic states in a subject as described above, processing may allow the detection of changes or transitions in other features of a signal captured from a subject which may be indicative of a state or event. For example, changes in any of the complexity, amplitude, phase, frequency, or any combination of such features (including in combination with a transition in coherence) may be used as indicators of a state or the occurrence of an event in a subject. The application of predetermined rules relating to such changes allows the detection of states or events. For example, a combination of changes in any of the above mentioned signal characteristics at a predetermined point in time, or within a predetermined time period, may be indicative of, for example, a physiological state in a subject. Further, the use of channelised signals may allow such detection to be carried out on a per channel basis, reducing the processing complexity. Alternatively, the application of a frequency-domain transform (e.g. FFT), or analysis of amplitude data across a broad range of frequencies also allows such event based detection.

For example, the presence of a signal component within a predetermined frequency band (e.g. 50 kHz±5 kHz) exhibiting a predetermined frequency shift (e.g. 1 kHz±0.5 kHz change per second), occurring for a predetermined period of time (e.g. 5 seconds) may be indicative of a known condition or response to a known stimulus.

Furthermore, rules may be based on a plurality of signal features, or a plurality of changes in signal features, occurring at a predetermined point in time, or within a predetermined time period. For example, rules may be based on logical combinations of detected events, allowing complex rules to be developed (e.g. a rule being based upon a plurality of sub-rules).

Processing arranged to implement event detection, and to apply detection rules, as described above, generates event identifiers. Such event identifiers may be grouped, for example, by the frequency bands in which they occur. Such groups of event identifiers may include, for example, the output of a process which detects a transition from a coherent signal to a chaotic signal, as described above with reference to FIG. 6.

The detection of events as described above, in particular time sequences of events, or transitions between states, can be combined to form Markov chains. Once Markov chains have been defined for a particular signal, or set of signals, further processing, for example using heuristic pattern based recognition, can be used as a diagnostic tool. For example a particular pattern of events or complex characteristics may be indicative of a condition (e.g. a medical condition). A database may be populated with known sequences of patterns in predetermined frequency bands, or using predetermined detection types (e.g. detection of coherent to chaotic transitions by a loosely coupled oscillator) which are consistent with known conditions. Detected sequences of events, or transitions between states, are subsequently processed to determine whether they are consistent with the known sequences of patterns stored in the database, and thus consistent with known conditions. A diagnosis may thus be generated based upon patterns in sequences of events being detected by the processing described above. Such processing can be carried out in real time (i.e. based on a signal as it is captured from a subject), or based on stored data.

It will be appreciated that the use of Markov chains is an example of a representation of transitions between distinct states. Other models can also be used to model the transitions between distinct states.

The processing described above to identify features in particular frequency bands of interest (e.g. for diagnostic purposes) allows data compression rates to be optimised for subsequent data storage. For example, the quantisation rate for particular frequency bands of interest can be selected so as to ensure data is preserved. On the other hand, quantisation rates for frequency bands which are of less significance can be selected so as to reduce the data storage requirements.

A further method of processing a signal which may contain particular components (whether desirable as donor signal components, or whether to be removed as noise components) is the use of software defined radio. Software defined radio allows a particular frequency component to be extracted from a signal by use of a radio in which processing, which in conventional radio is carried out by analogue components, is carried out by software running on a processor. Such a configuration allows a single processor to process signals at a variety of different frequencies without having to have specific analogue hardware components which are targeted at each of those frequencies.

Figure 7:
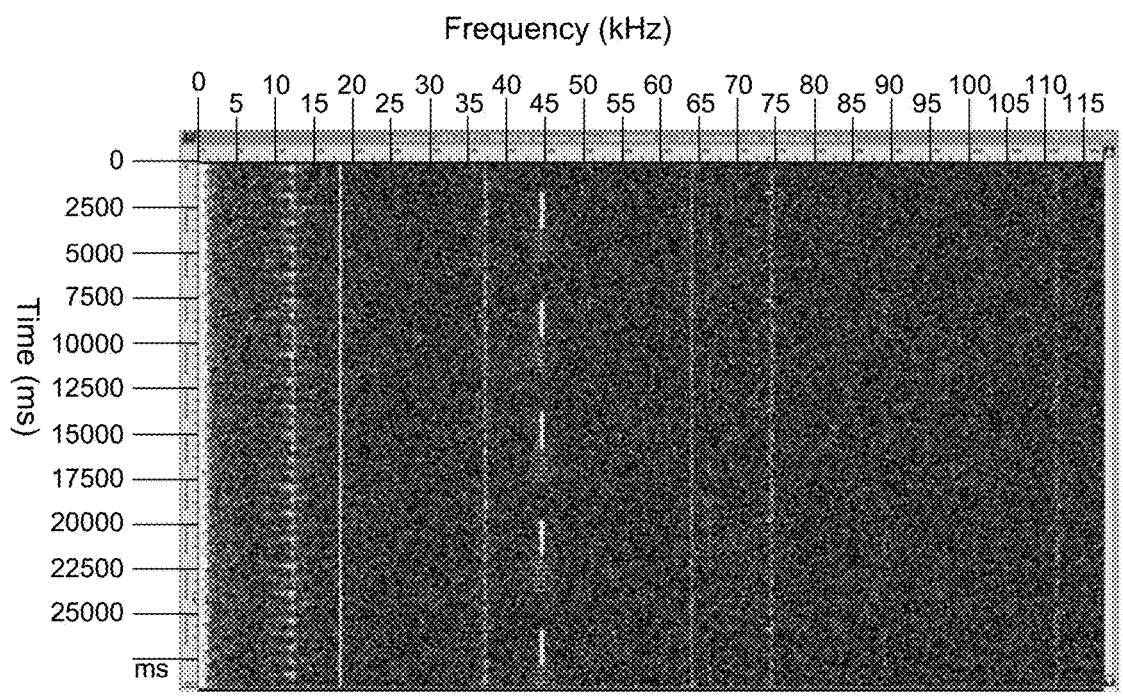
FIG. 7 illustrates signals captured by the system shown in FIG. 1.

FIG. 7 shows data captured using embodiments of the invention described above with reference to FIGS. 1 to 4. The displayed data relates to data captured without a subject being present (i.e. the data represents external noise sources only) and is displayed as a plot of frequency (horizontal axis, increasing frequency left to right) against time (vertical axis, increasing top to bottom). The shading of the image represents the power density at each frequency. It can clearly be seen that at certain frequencies repeating patterns are visible. For example, noise sources are present at around 12, 18, 37, 44, 67.5, 74 and 111 kHz.

Figure 8:
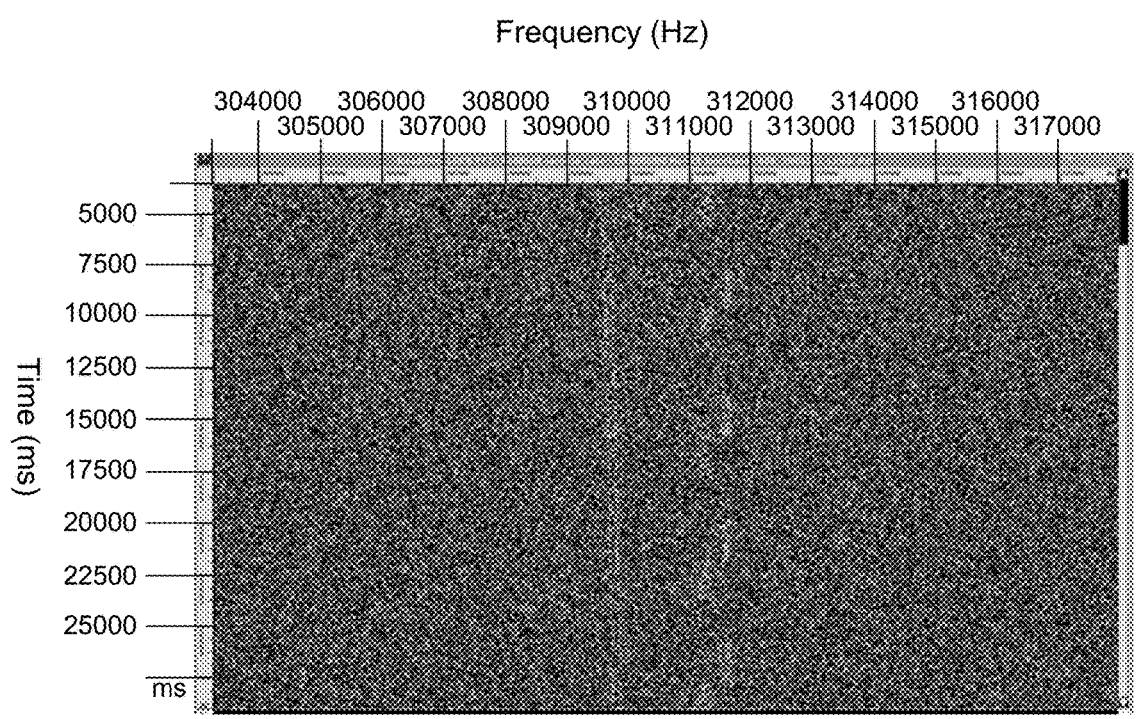
FIG. 8 illustrates further signals captured by the system shown in FIG. 1.

FIG. 8, shows data captured using embodiments of the invention described above with reference to FIGS. 1 to 4. The displayed data relates to data captured from a human subject (i.e. the data represents internal signal sources only) and is displayed as a plot of frequency (horizontal axis, increasing frequency left to right) against time (vertical axis, increasing top to bottom). Again, the shading of the image represents the power density at each frequency. It can clearly be seen that at certain frequencies repeating patterns are visible. For example, signal sources are present at around 309.5 and 311.5 kHz.

Figure 9:
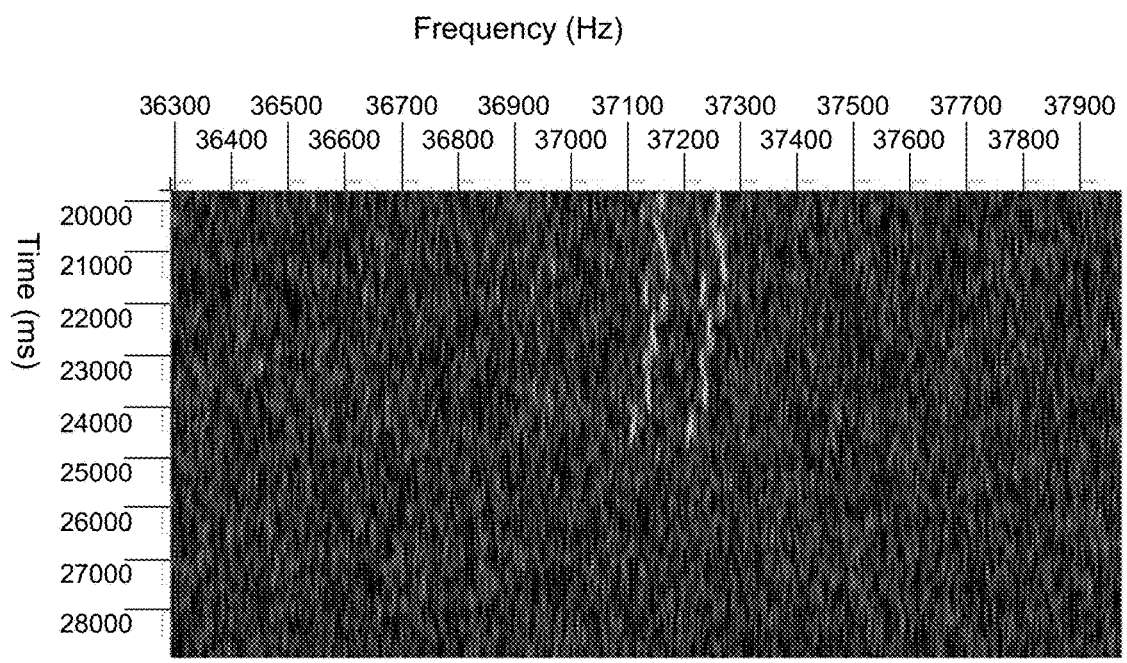
FIG. 9 illustrates further signals captured by the system shown in FIG. 1.

FIG. 9, shows data captured using embodiments of the invention described above with reference to FIGS. 1 to 4. The displayed data relates to data captured both from a human subject (i.e. representing internal signal sources) and without a human subject being present (i.e. representing external noise sources) and is displayed as a plot of frequency (horizontal axis, increasing frequency left to right) against time (vertical axis, increasing top to bottom). Again, the shading of the image represents the power density at each frequency. The data displayed is the combination of two recordings, one with, and one without a human subject. At approximately half-way through the recording the data captured from the human subject stops, and what continues is contributed by external noise sources. It can clearly be seen that, until that point, at certain frequencies repeating patterns are visible. For example, signal sources are present at around 37.15 and 37.25 kHz. These signal sources are from the human subject.

Figure 10:
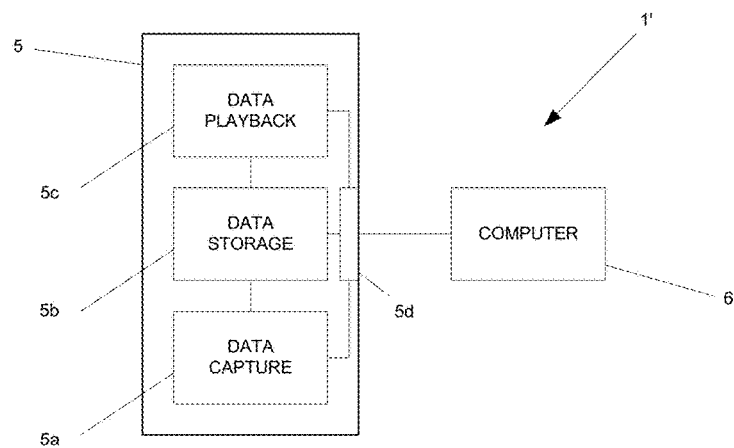
FIG. 10 illustrates an apparatus for processing signals.

FIG. 10 shows an apparatus 1'. The apparatus 1' comprises a treatment device 5 and a computer 6. The treatment device 5 comprises a data capture device 5a, a data storage device 5b, a data playback device 5c and an interface device 5d. The treatment device 5 is connected to the computer 6 via the interface device 5d.

The data capture device 5a is similar to the data capture device 1h described above with reference to FIG. 2. The data storage device 5b may be any suitable form of storage device which is capable of storing the digital signals which are output from the data capture device 5a. The data storage device 5b may, for example, be a hard disk drive or a solid state drive which is capable of meeting the data storage requirements of the data capture device 5a (i.e. data capacity and data capture rate). The data playback device 5c is similar to the data playback device 1i described above with reference to FIG. 2.

Signals captured by the data capture device 5a may be stored in the storage device 5b. The data playback device 5c may be configured to playback signals stored in the storage device 5b via a cable and electrodes to a subject.

The data capture device 5a, data storage device 5b, and data playback device 5c may be operated under the control of the computer 6. For example, the treatment device 5 maybe connected to the computer 6 by a USB cable, or by a wireless connection (e.g. Bluetooth). The computer 6 may be any convenient form of computing device. For example, the computer 6 may be a desktop computer, a laptop computer, a tablet computer, a mobile telephone, or any other appropriate device.

Figure 11:
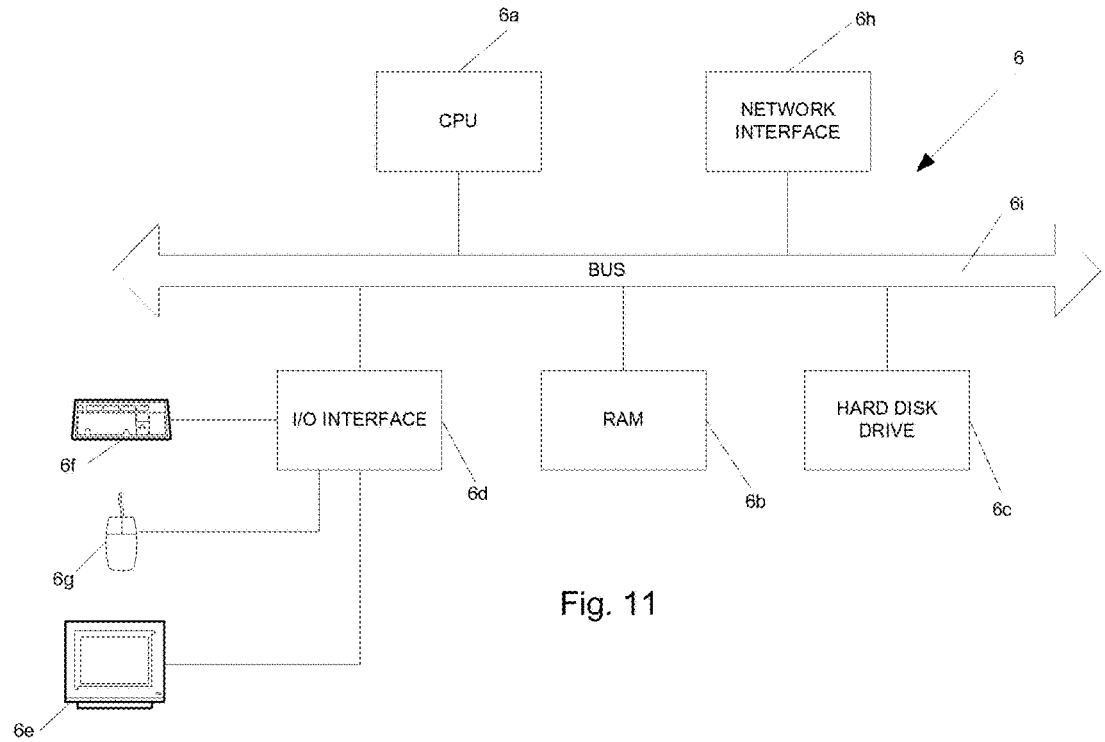
FIG. 11 illustrates a part of the apparatus shown in FIG. 10 in more detail.

FIG. 11 shows the computer 6 in more detail. The computer 6 comprises a CPU 6a which is configured to read and execute instructions stored in a volatile memory 6b which takes the form of a random access memory. The volatile memory 6b stores instructions for execution by the CPU 6a and data used by those instructions. For example, in use, data relating to a treatment program for a subject may be stored in the volatile memory 6b.

The computer 6 further comprises non-volatile storage in the form of a hard disc drive 6c. The data relating to a treatment program may be stored on the hard disc drive 6c. The computer 6 further comprises an I/O interface 6d to which are connected peripheral devices used in connection with the computer 6. More particularly, a display 6e is configured so as to display output from the computer 6. The display 6e may, for example, display a representation of the treatment program. Additionally, or alternatively, the display 6e may display a representation of signals generated by processing of signals received from the treatment device 5. Input devices are also connected to the I/O interface 6d. Such input devices include a keyboard 6f and a mouse 6g which allow user interaction and control of the computer 6. The computer 6 may be connected to the treatment device 5 via the I/O interface 6d.

It will be appreciated that where the computer is not a conventional desktop computer alternative or additional input and display devices may be provided. For example, where the computer 6 is a mobile telephone or tablet computer, the device's screen may serve as both display and input device (i.e. replacing the mouse and keyboard with a touch screen). Of course, such a device may additionally be provided with a separate keyboard and/or mouse should such input devices be required. Further, the computer 6 may not require conventional input devices.

A network interface 6h allows the computer 6 to be connected to an appropriate computer network so as to receive and transmit data from and to other computing devices. The network interface 6h may be configured to allow the computer 6 to receive and transmit data via a wired or wireless network. The computer 6 may also be configured to be connected to the treatment device 5 via the network interface 6h. The CPU 6a, volatile memory 6b, hard disc drive 6c, I/O interface 6d, and network interface 6h, are connected together by a bus 6i.

In use, the treatment device 5 may be controlled by the computer 6 to record signals from a subject. The treatment device 5 may store (and optionally process) the signals, as described above with reference to FIG. 3. The treatment device 5 may also be controlled by the computer 6 to playback (and optionally process) signals to a subject, as described above with reference to FIG. 4. The signals played back to a subject may be signals which were earlier recorded from the subject. Alternatively, the played back signals may be signals which are provided to the treatment device 5 from an external source, for example via the computer 6.

A subject who is receiving treatment is able to receive step by step help on the use of the apparatus 1'. For example, the subject 2 is able to receive step by step help on the use of the treatment device 5 from a software application running on the computer 6 Signals which are captured and/or stored by the apparatus may be transmitted for further processing, and/or storage via the network interface 6h.

The treatment device 5 and computer 6 may be portable, so as to allow treatment in any convenient location. The treatment device 5 may further operate in isolation (i.e. without a connection to the computer 6). That is, operation of a treatment device does not require connection to a network.

Figure 12:
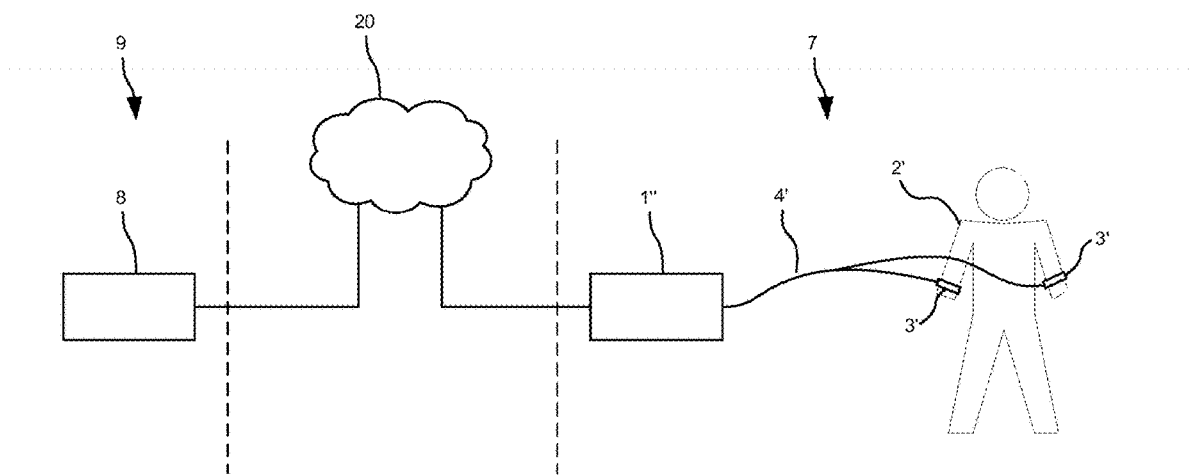
FIG. 12 illustrates an alternative system for processing signals.

A further embodiment of the invention is illustrated in FIG. 12. An apparatus 1″ is provided at a treatment location 7. The apparatus 1″ may be an apparatus 1 as described above with reference to FIGS. 1 and 2. Alternatively, the apparatus 1″ may be an apparatus 1' as described with reference to FIG. 10 (either the treatment device 5 or the treatment device 5 in combination with the computer 6). The apparatus 1″ is arranged to capture and/or deliver signals from/to a subject 2 via electrodes 3 and cables 4 (which are also as described above with reference to FIG. 1). The signals captured from and/or delivered to a subject 2 may be processed as described above with reference to FIGS. 3 and 4.

The treatment location 7 may be any location at which it is convenient to deliver a treatment. For example, the treatment location 7 may be the home of the subject 2. Alternatively, treatment location 7 may be a local treatment centre.

A server 8 is provided at a service location 9, which is remote from the treatment location 7. The server 8 may be any convenient form of computing device. For example, the server may be a computer as described with reference to FIG. 11. The server may, for example, be a mainframe computer. The server may be accessed by skilled operators.

The service location 9 may be any location at which it is convenient to store and/or process data in connection with a treatment. The service location 9 may, for example, be a treatment centre, or a remote service centre. Communications with the service location 9 may be carried out by various means, such as, for example, email, telephone or the Internet.

The apparatus 1″ is connected to the server 8 via a network 20. In an embodiment the network may, for example, be the Internet. It will be appreciated that any form of connection between the apparatus 1″ and the server 8 may be used.

In the system of FIG. 12, any or all of the processing tasks described above as being carried out within the apparatus 1″ (and therefore any or all of the processing described above with reference to the apparatus 1 and 1') may be carried out within the server 8. Further, the server 8 may be arranged to control the apparatus 1″ to capture or playback signals from/to the subject 2.

In particular, in the system of FIG. 12, the server 8 may be arranged to monitor the capture or playback of signals. Further, the server 8 may be arranged to process, analyse, store, or synthesise signals for use in treatment of a subject either in real-time, or for past or future treatments as appropriate.

In an embodiment the subject 2, who is receiving treatment at the treatment location 7 (e.g. their home), is able to receive support from skilled operators at the service centre 9. The skilled operators are able to monitor the capture and/or playback of signals via the server 9. The subject 2 may communicate with the skilled operators via a communications channel which is provided by the apparatus 1″. For example, where the apparatus 1″ is the computer 6 (e.g. a mobile telephone) in combination with the treatment device 5, the subject 2 is able to communicate with the skilled operators via text, video and/or voice communications. The subject 2 may receive step by step help on the use of an apparatus from the skilled operators. The subject 2 may receive help with dosage from the skilled operators. The subject 2 may receive advice, for example health advice, in connection with their treatment from the skilled operators In an embodiment the subject 2, who is receiving treatment at the treatment location 7 (e.g. their home), is able to access data associated with their treatment which is stored on the server 8 at the service centre 9. The data may, for example, comprise historical health information associated with the subject 2. For example the data may comprise a treatment history of the subject 2. The server 8 may further store signals from a subject or a plurality of subjects. The server may store signals which are characteristic of a particular condition (e.g. a signature signal), or which are of particular use in the treatment of a particular condition (e.g. for reference purposes).

A skilled operator, who is providing treatment to the subject 2 at the treatment location 7 (e.g. a local treatment centre), is able to access data associated with the treatment which is stored on the server 8 at the service centre 9. The data may be any data associated with the subject 2 (e.g. historical health information).

The subject, or the skilled operator, may use the apparatus 1″ (e.g. the computer 6), to initiate capture of a signal being emitted by the subject, or to request the playback of a previously stored signal (which may or may not have been processed). The apparatus 1″ may then record additional data such as, for example, skin conductivity or heart rate during any subsequent capture or playback, allowing the additional data to be associated with the delivered treatment in a treatment record.

The subject, or the skilled operator, may input further health indicators (e.g. weight, body mass index) via the apparatus 1″, so that these further health indicators are associated with a treatment record. A skilled operator may analyse or process a signal to generate a diagnosis, or to derive a signal for treatment of a condition.

Signals detected from a subject by electrodes may be processed before being captured by a data capture device. For example, the analogue signals may be amplified prior to capture and digitisation. Further, any of the processing described above which is carried out by an apparatus according to embodiments of the invention (e.g. filtering, looping, sampling, noise reduction etc.), or by a processor within a server, may be carried out by analogue electronics prior to signals being captured and digitised. Similarly, any of the processing described above which is carried out by an apparatus according to embodiments of the invention, or by a processor within a server, may be carried out by analogue electronics after a signal is played back by a data playback device. For example, an analogue processing unit may be provided which is connected between the electrodes and the data capture and/or playback device.

It will further be appreciated that where processing is described as being carried out by a processor such as a CPU, any appropriate form of processor may be used. For example, signals may also be processed by GPUs, multi-core and many-core processor units, programmable logic devices such as field programmable gate arrays (FPGAs) or digital signal processors (DSP). Signals may also be processed or pre-processed by external analogue or digital computing elements, such as, for example, an artificial neural network.

A data capture device (e.g. the data capture device 5*a*) and a data playback device (e.g. the data playback device 5*c*), described above as separate devices, may be provided within a single device. For example, a capture/playback device may be configured to have a high input impedance during capture, and a high output impedance during playback. Further, while a treatment device (e.g. the treatment device 5) is described above as comprising a capture device and a playback device, a treatment device according to an embodiment may comprise only a capture device or a playback device. This may be especially useful for portable treatment (e.g. treatment which is carried out at a subject's home) where only one of data capture or playback is required to be carried out.

It will be appreciated that where a plurality of electrodes are described, where appropriate, a single electrode may be used to deliver and/or capture a signal.

It will be further be appreciated that where electrodes are described as being capable of both capture and playback, in some embodiments separate electrodes may be used for capture and playback.

It will be further be appreciated that where a single cable is described as connecting an apparatus to electrodes for both capture and playback, in some embodiments separate cables may be used for capture and playback (either with separate electrodes for capture and playback, or combined capture/playback electrodes). Further, cables may also be configured to transfer signals generated by other sensors which may be present in an electrode, or in a secondary electrode.

Embodiments of the invention are described above, primarily with reference to a human subject. However, it will be appreciated that signals may also be captured from or delivered to animal subjects. Furthermore, animal subjects may provide signals for use with human subjects. For example, signals may be captured from a pet (i.e. the pet being a signal donor), and subsequently played-back to the pet's owner (i.e. a human subject) in order to bring about some beneficial effect. Furthermore, it will be appreciated that any biological source may be used as a signal donor.

The described and illustrated embodiments are to be considered as illustrative and not restrictive in character, it being understood that only preferred embodiments have been shown and described and that all changes and modifications that come within the scope of the invention as defined in the claims are desired to be protected. In relation to the claims, it is intended that when words such as "a," "an," "at least one," or "at least one component" are used to preface a feature there is no intention to limit the claim to only one such feature unless specifically stated to the contrary in the claim. When the language "at least a component" and/or "a component" is used the signal can include a component and/or the entire signal unless specifically stated to the contrary.

Optional and/or preferred features as set out herein may be used either individually or in combination with each other where appropriate and particularly in the combinations as set out in the accompanying claims.

The Following Provides Further Information Relating to Some Embodiments of the Invention. This Description should be Considered Entirely Separately to that Set Out Above, as Well as in Combination Therewith.

Therapeutic Methods Using the Recording and Playback of High-Bandwidth Electrical Signals from the Body

SUMMARY

This document describes a general method for electroceutical therapies for the treatment of a variety of health and wellness conditions by recording high bandwidth electrical voltage signals from an animal or person and by replaying those signals to the same or similar individuals.

Many conditions may be treated including, but not limited to, sleeplessness, high blood pressure, weight reduction, pain relief, migraine and depression. If, for example, an individual is suffering from sleeplessness a recording would be made of the electrical signals while the individual was asleep and the signal would be replayed to them at a later date to help them go to sleep. Similarly, another example, a weight loss therapy would involve the repeated playback over a period of time of a recording made while the individual was exercising.

Method

Figure 13:
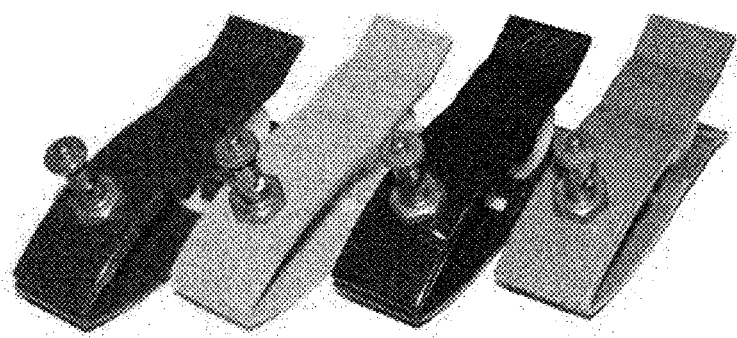
FIG. 13 illustrates electrodes which may be used for capturing and playing back signals.

One method includes one or more of three logical steps.
1. Recording the signal
2. Processing the stored signal
3. Playback of the signal to the patient Recording Recoding takes place by attaching to the patient an electrode which is, in turn connected to the recording device. In one embodiment, the electrodes can be similar to the simple electrodes used for measurements of ECG or EEG apparatus (for example see FIG. 13). A signal representative of the measured voltage can be sent to the recording device by a low loss RF cable, for example. Signals recorded with this kind of electrode typically have a peak-to-peak voltage of less than 3V, although other signal parameters are possible. The recording device may include a high input impedance, high speed data capture card. In one embodiment, the capture card is capable of sampling at typically 100 million samples per second with an analog-to-digital conversion resolution of typically 16 bits. The data card is connected to a storage device capable of matching the very high data capture rates required. The storage device may be a hard disk drive or any other data storage mechanism that meets the speed and capacity requirements of data capture. The recording devices are typically connected to mains power and are cooled with fans. In a representative embodiment, recordings last 5 minutes, but the recording time is ultimately determined by the effect desired In one embodiment, the recording device can be data-connected to facilitate remote monitoring. The data connection can be via an internet, intranet, or other available protocol. The remote monitoring can be performed at a network operating centre where skilled staff may monitor the patient and help with the recording process. Alternatively, the recording device may also be controlled using a portable device, such as a smart phone application. Among other features, such portable device and/or application might also provide the patient with step by step help on the use of the device. Moreover, the portable device/application might also be used for direct communication between the patient and skilled staff at the network operating centre using voice, text and video communication.

The electrode used for recording can also be equipped with other monitoring devices capable of recoding patient parameters which might include, but not be limited to, skin temperature, pulse rate, blood oxygen level, skin conductivity and blood pressure. These additional parameters that may be measurable by the electrode may also be converted into digital form, then sent to and stored by the recording device or at the network operating centre.

Processing

The recorded and digitized voltages may be played back as recorded or subject to processing before playback. Such processing methods include, but are not limited to, sampling, amplification, noise reduction, splicing, frequency filtering and looping.

For many conditions such as sleeplessness and weight loss a high bandwidth, unprocessed signal may be played back as there are several changes in the body between the current and desired state (i.e. asleep and awake or slow metabolic rate and higher metabolic rate) and a high bandwidth signal may be more effective at inducing the desired state.

The recordings may be processed locally or may be uploaded to the network management centre for processing.

Playback

Playing back a signal involves attaching an electrode to a patient as described above and then connecting to the playback device. The same electrode may be used for recording and playing back the signal. Connection to the playback device may be by a low loss RF cable. In one embodiment, signals being played back have a peak to peak voltage of less than 6V, but other signal characteristics are possible. In one embodiment, the playback device is the same apparatus as used for recording but in playback mode it will consist of high output impedance, high speed data playback card capable of playing at typically 100 million samples per second with an digital to analogue conversion resolution of typically 16 bits. Other sample rates, resolution values, and peak-to-peak voltages are also possible. This device may be connected to a network and the Internet and may also be connected to mains power and may be cooled by a fan. The signal may be looped (played over and over) for a period of time depending on the condition being treated. During playback the patient may be monitored and any reactions noted.

The playback device may be capable of remote monitoring from a network operating centre where skilled staff may monitor the patient and help with the dosage of the electroceutical therapy and provide other health advice. The playback device may also be partially controlled by the patient using a portable device and/or application. This application may also guide the patient and provide historical medical data.

In one embodiment, the signal utilized during playback for a given patient is based on a recording made from the same patient. In such embodiment, the signal may or may not have been processed prior to playback. Alternatively, the signal utilized during playback may be based on a recording made from a different subject. Moreover, the signal utilized during playback may be based on a recording made from a subject other than the patient, but who shares one or more characteristics with the patient.

Apparatus

The apparatus consists of five main logical elements:
1. Electrodes
2. Recording device
3. Computer software and hardware for signal recording, processing and playback
4. Playback device
5. Network management centre including database of recorded parameters and treatments and skilled staff to help and advise the patient.

Figure 14:
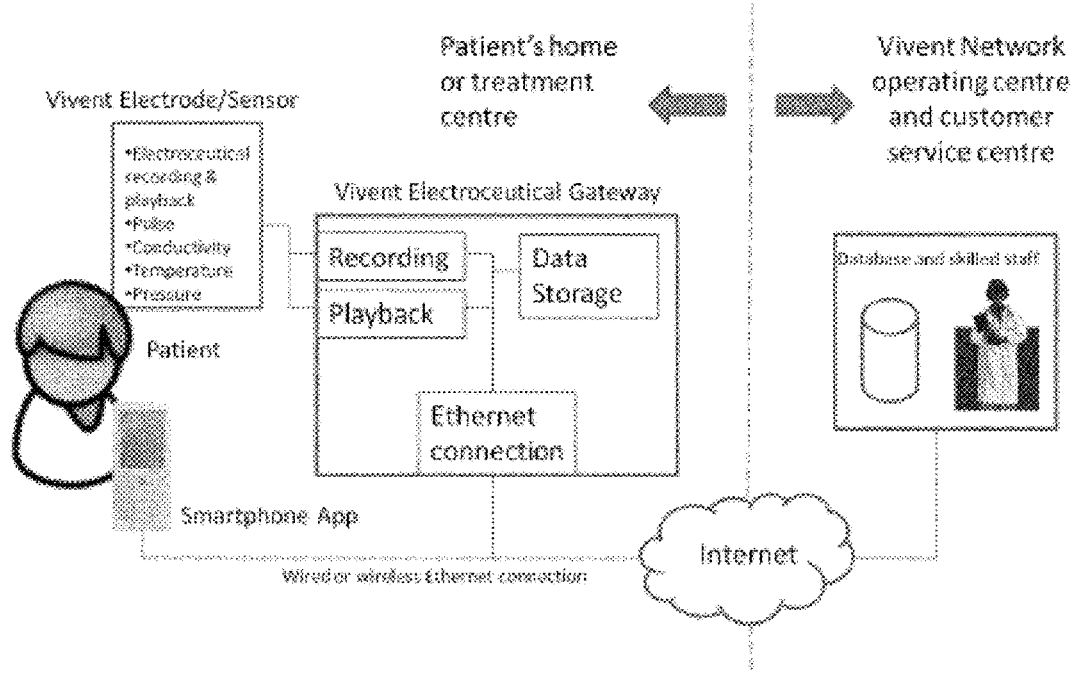
FIG. 14 illustrates an alternative system for processing signals.

These elements are linked as shown logically in FIG. 14. In one embodiment, the first four are combined in a single package, the Vivent Electroceutical Gateway, which is considered a Type 2 medical device.

Electrode

Figure 15:
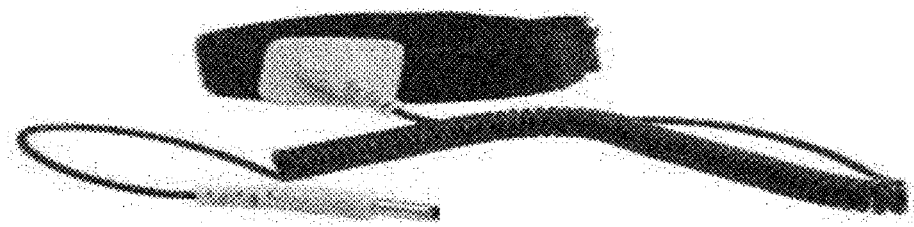
FIG. 15 illustrates an electrode which may be used for capturing and playing back signals.

In an embodiment, the electrode includes a connector that attaches to the recording and/or playback device, a low loss RF cable and an elasticised band that can be worn around the wrist or ankle. An example of a typical electrode is shown in FIG. 15. Embedded in the elasticised band are an electrode for recording and transmitting the electrical signal and optionally one or more of a number of sensors, including but not limited to: skin temperature probe, skin conductivity probe, pulse rate measurement device, blood oxygen level measurement device and a blood pressure measurement device.

Vivent Electroceutical Gateway

The Vivent Electroceutical Gateway currently resembles a desk top computer hard drive and in the future will resemble a small electronic device such as an iTV. A metal or plastic box houses the electronics and can be connected to mains power through a power cable, to the electrode through a press fit connection and to data networks through WiFi or standard network connectors.

It comprises a recording device consisting of a high input impedance, high speed data capture card capable of sampling at typically 100 million samples per second with an analogue to digital conversion resolution of typically 16 bits. The data card is connected to a storage device of one or more hard disk drives capable of matching the very high data capture rates required.

The playback device comprises a high output impedance, high speed data playback card capable of playing at typically 100 million samples per second with an digital to analogue conversion resolution of typically 16 bits.

The Vivent Electroceutical Gateway is connected to an information network and the Internet and may also be connected to mains power and may be cooled by a fan.

In-house developed software is used to drive the processes of recording, manipulating and playing back the electrical signals emitted by the patient. This software has been developed using industry standard languages and is documented in manner that is acceptable for quality control assurances.

Sample Smartphone Application

Patients may access treatments through a Smartphone application or by contacting the network operating center. The Smartphone application enables patients or approved therapists to contact the Network Operating Center and to request historical health information, to demand a recording of the current electrical signature being emitted by the patient or to playback a preciously recorded and/or manipulated electrical signature of the same patient. The Smartphone application will record therapeutic treatments and the corresponding health indicators such as heart rate or skin conductivity. It will also be possible for the patient to input certain health indicators such as weight or body mass index to keep track of changes to these indicators over time.

Network Operating Centre

The Network Operating Centre is staffed by trained health and administration professionals. The purpose is to advise clients and/or medical professionals on the application of Vivent electroceutical therapies.

The Network Operating Centre will house mainframe computers on which patient records, electrical signatures and administrative data is stored. Access to the centre will be through telephone, email and smartphone applications. Trained individuals will generate responses to patient queries and as well as determining appropriate therapeutic treatments including the manipulation of individual electrical signatures.

Services

Testing

The objective of clinical trials associated with Vivent Electroceutical therapies are to demonstrate proof of delivery of benefits for a target population within legal and scientifically rigorous trial conditions. The efficacy of the therapies is studied using either single or double blind crossover trials involving typically 8 or more participants. A cross-over design where each person is exposed to the real signal playback and a placebo signal playback during each of 2 testing periods which normally last 3 weeks minimum for each period is deemed the most rigorous trial design. Double blind is the more rigorous protocol, with prototype 'codes' being broken at the end of the study/analysis and is used whenever possible.

The types of claims under consideration, in this case for the weight management therapy, include but are not limited to:

Aids weight loss alongside regular exercise & dietary control, after X weeks of use.

Boosts weight loss by Y % over a period of X weeks of use, alongside regular exercise & dietary control.

Areas of Potential Patent Claims
1. Treatment using high frequency analogue or fast switching digital electrical signals
2. Treatment using signals harvested from living people (animals)
3. Treatment of an individual based on signals harvested from that individual or a genetically similar individual.
4. Delivery of electroceuticals remotely over the Internet
5. Control of treatments using electroceuticals over the Internet A system for recording electrical signals from a subject, and playing back the electrical signals to a patient, comprising:
  a recording electrode structured to detect an electrical signal from the subject;
  a data storage device logically connected to the electrode so as to allow the data storage device to store data representative of the electrical signal; and
  a playback electrode logically connected to the data storage device, the playback electrode being structured and arranged so as to play back the electrical signal to the patient.

Any of the systems above, wherein the recording electrode and the playback electrode are a single device.

Any of the systems above, further comprising a digital-to-analog converter (ADC) that receives an analog version of the electrical signal from the electrode and converts the analog electrical signal into a digital electrical signal that is stored on the data storage device.

Any of the systems above, wherein the recording electrode is structured and arranged to make contact with skin of the subject.

Any of the systems above, wherein the playback electrode is structured and arranged to make contact with skin of the patient.

Any of the systems above, further comprising a processor structured and arranged to process the data representative of the electrical signal prior as part of, or subsequent to, recording of the data representative of the electrical signal.

Any of the systems above, further comprising monitoring devices structured to detect patient parameters.

The system above, wherein the parameters include one or more of skin temperature, pulse rate, blood oxygen level, skin conductivity and blood pressure.

The system above, wherein at least one of the detected parameters is stored.

Any of the systems above, further comprising a remote management center, wherein the data representative of the electrical signal is stored at the remote management center.

Any of the systems above that includes the processor and the remote management center, wherein the processor is located at the remote management center.

Any of the systems above that includes the remote management center, wherein operation of the playback electrode is controlled at the remote management center.

A method for administering a therapy to a patient, comprising steps of:
  recording an electrical signal from a subject;
  storing the electrical signal; and
  playing back the stored electrical signal to a patient.

Any of the methods above, wherein the subject and the patient are a single person.

Any of the methods above, wherein at least one of the recording step and the playback step is performed using an electrode.

The method above, wherein the electrode is in contact with skin of the subject and/or patient.

Any of the methods above, further comprising a step of analog-to-digital conversion (ADC) between the recording and storing steps, and digital-to-analog conversion (DAC) between the storing and playing back steps.

Any of the methods above, comprising a further step of processing the electrical signal from the subject prior to the playing back step.

The method above, wherein the processing step comprises at least one of sampling, amplification, noise reduction, splicing, frequency filtering and looping.

Any of the methods above, further comprising a step of monitoring patient parameters during at least one of the recording and playing back steps.

The method above, wherein the parameters include one or more of skin temperature, pulse rate, blood oxygen level, skin conductivity and blood pressure.

The method above, further including a step of storing at least one of the detected parameters.

Any of the methods above, wherein the storing step is performed at a remote management center.

Any of the methods above that includes the processing step and the remote management center, wherein the processing is performed at the remote management center.

Any of the methods above that includes the remote management center, wherein the playing back step is controlled at the remote management center.

The invention claimed is:

1. An apparatus comprising:
  an electrical signal sensor configured to obtain one or more first input signals from first one or more human or animal subjects when the first one or more human or animal subjects are in a particular state being selected from the group consisting of an emotional state, a metabolic state, a physical state or a physiological state;
  a secondary sensor, wherein the secondary sensor is configured to obtain a secondary input signal from the first one or more human or animal subjects, the secondary input signal being indicative of said state of the first one or more human or animal subjects;
  an electrical signal stimulus device, wherein the electrical signal stimulus device is configured to deliver an electrical signal stimulus to said first one or more human or animal subjects while the electrical signal sensor obtains the one or more input signals from said first one or more human or animal subjects;

an electrical signal generation device configured to receive said one or more first input signals from said electrical signal sensor and said secondary input signal from said secondary sensor, the electrical signal generation device being further configured to generate a processed input signal by processing said one or more first input signals;

a memory associated with the electrical signal generation device configured to store instructions to cause the electrical signal generation device to generate the processed input signal by processing said one or more first input signals; and an electrical signal application device comprising an electrode and a cable, wherein the electrical signal application device is configured to receive the processed input signal from the electrical signal generation device and to apply the processed input signal, via the electrode and the cable, to a second human or animal subject so as to induce the particular state within the second human or animal subject.

2. An apparatus according to claim 1 wherein the apparatus is configured to receive a plurality of input signals, each of said plurality of input signals being a signal captured from a respective one of a plurality of subjects, each of said plurality of input signals being obtained by an electrical signal sensor.

3. An apparatus according to claim 2 wherein each of the plurality of subjects has a common characteristic, and the electrical signal generation device is configured to generate the processed input signal by extracting a signal indicative of the common characteristic from the plurality of input signals.

4. An apparatus according to claim 1, wherein processing the one or more input signals comprises filtering at least one of the one or more input signals.

5. An apparatus according claim 1, wherein processing the one or more input signals comprises combining component signals derived from the one or more input signals, wherein combining the component signals comprises looping the component signals and/or playing the component signals concurrently, wherein each of the component signals corresponds to a sample of the one or more input signals at a respective point in time.

6. An apparatus according to claim 1, wherein processing the one or more input signals comprises:
receiving a plurality of components of the signal, wherein each of the plurality of components corresponds to a sample of the signal at a respective point in time;
detecting a phase of the signal;
populating a plurality of elements of an output buffer, each element being populated with a respective one of a plurality of output signal components, each of the plurality of output signal components being based upon one or more of the plurality of components of the signal; and
generating a plurality of indices for the output buffer based upon the detected phase;
wherein the processed input signal comprises a plurality of output signal components based upon said plurality of indices.

7. An apparatus according to claim 1, wherein the electrical signal sensor is configured to obtain an input signal from the first human or animal subject and the electrical signal application device is configured to apply the processed input signal to said second human or animal subject which is the same as the first human or animal subject.

8. An apparatus according to claim 1, wherein the electrical signal application device is configured to apply said processed input signal to the second human or animal subject, the second human or animal subject being different from said first one or more human or animal subjects.

9. An apparatus according to claim 1, further comprising a wide area network interface coupled to said electrical signal generation device, said wide area network interface being arranged to transmit said processed input signal to said electrical signal application device.

10. An apparatus according to claim 1, further comprising a wide area network interface coupled to said electrical signal generation device wherein said electrical signal sensor is arranged to provide said input signal to said electrical signal generation device via said wide area network interface.

11. An apparatus according to claim 10, further comprising a plurality of signal sensors each arranged to provide an input signal to said electrical signal generation device via said wide area network interface.

12. An apparatus according to claim 1, further comprising an electrical signal capture device wherein the electrical signal capture device is configured to convert the one or more input signals into one or more digital signals.

13. An apparatus according to claim 1, wherein the electrical signal application device further comprises a digital to analogue convertor configured to convert the processed input signal from a digital signal to an analogue signal.

14. An apparatus according to claim 1, wherein the processed input signal comprises a synthesised signal, wherein the synthesised signal is modelled based upon the one or more input signals generated from the first one or more human or animal subjects.

15. An apparatus according to claim 14, wherein the synthesised signal is modelled based upon the data relating to the first one or more human or animal subjects.

16. An apparatus according to claim 1, further comprising a monitor interface configured for connection to a monitor device, wherein the monitor interface is configured to generate an output which is indicative of the processed input signal or the one or more input signals.

17. An apparatus according to claim 16, wherein the monitor device is a display device and the output comprises display data.

18. An apparatus according to claim 1, wherein the one or more input signals are selected from the group consisting of electroencepthalography data, electrocardiogram data, temperature data, conductivity data, heart rate data, blood oxygen data and blood pressure data.

19. An apparatus according to claim 1, wherein the electrical signal stimulus device is configured to generate an electrical signal stimulus comprising a frequency sweep and/or a substantially constant power spectral density within a predetermined frequency band.

20. An apparatus according to claim 1, further comprising a software defined radio, the software defined radio comprising a processor which is configured to carry out processing of extracting a particular frequency component from a signal, the software defined radio being configured to process the one or more input signals so as to extract one or more signals having a predetermined frequency component, the processed input signal being based upon said one or more signals having a predetermined frequency component.

* * * * *